(12) United States Patent
Bukesov et al.

(10) Patent No.: US 11,406,449 B1
(45) Date of Patent: Aug. 9, 2022

(54) OPTICAL SPLITTER FOR LASER SURGICAL SYSTEMS WITH OVERHEATING PROTECTION

(71) Applicant: GYRUS ACMI, INC., Westborough, MA (US)

(72) Inventors: Sergey A. Bukesov, Acton, MA (US); Kurt G. Shelton, Bedford, MA (US)

(73) Assignee: Gyrus ACMI, Inc., Westborough, MA (US)

( * ) Notice: Subject to any disclaimer, the term of this patent is extended or adjusted under 35 U.S.C. 154(b) by 0 days.

(21) Appl. No.: 17/376,908

(22) Filed: Jul. 15, 2021

Related U.S. Application Data

(60) Provisional application No. 63/171,636, filed on Apr. 7, 2021.

(51) Int. Cl.
*A61B 18/20* (2006.01)
*A61B 90/00* (2016.01)
*A61B 18/00* (2006.01)

(52) U.S. Cl.
CPC .............. *A61B 18/20* (2013.01); *A61B 90/04* (2016.02); *A61B 2018/00577* (2013.01); *A61B 2018/00791* (2013.01); *A61B 2018/00982* (2013.01); *A61B 2018/20553* (2017.05); *A61B 2090/049* (2016.02); *A61B 2090/0454* (2016.02)

(58) Field of Classification Search
CPC ......... A61B 18/20; A61B 18/22; A61B 18/24; A61B 18/201; A61B 2018/2005; A61B 2018/2035; A61B 2018/20361; A61B 2018/20553; A61B 2018/205547; A61B 2018/208; A61B 2018/00982; A61B 2018/00577; A61B 2018/00791; A61B 90/04; A61B 2090/0454; A61B 2090/049
USPC ........ 606/15–17, 33, 41, 34, 38, 42; 607/88, 607/89
See application file for complete search history.

(56) References Cited

U.S. PATENT DOCUMENTS

| | | | | |
|---|---|---|---|---|
| 5,057,099 | A * | 10/1991 | Rink ...................... | A61B 18/20 606/12 |
| 6,323,457 | B1 * | 11/2001 | Jung .................... | B23K 26/702 219/121.62 |
| 2002/0022829 | A1 * | 2/2002 | Nagase .................. | A61B 18/20 606/12 |

\* cited by examiner

*Primary Examiner* — Thomas A Giuliani
(74) *Attorney, Agent, or Firm* — Schwegman Lundberg & Woessner, P.A.

(57) ABSTRACT

Systems, devices, and methods for identifying a target in vivo are disclosed. A target identification system for use in electrosurgery includes a probe, an optical splitter, and a spectroscopy system. The probe includes an optical pathway to pass a first optical signal to an anatomical target and at least a portion of a second optical signal from the anatomical target. The optical splitter includes a first port to direct the first optical signal to the optical pathway and to receive the at least a portion of the second optical signal from the optical pathway, a second port to receive the first optical signal, and a parabolic reflector to redirect the portion of the second optical signal. The spectroscopy system can identify a characteristic of the anatomical target based on the redirected at least a portion of the second optical signal.

15 Claims, 9 Drawing Sheets

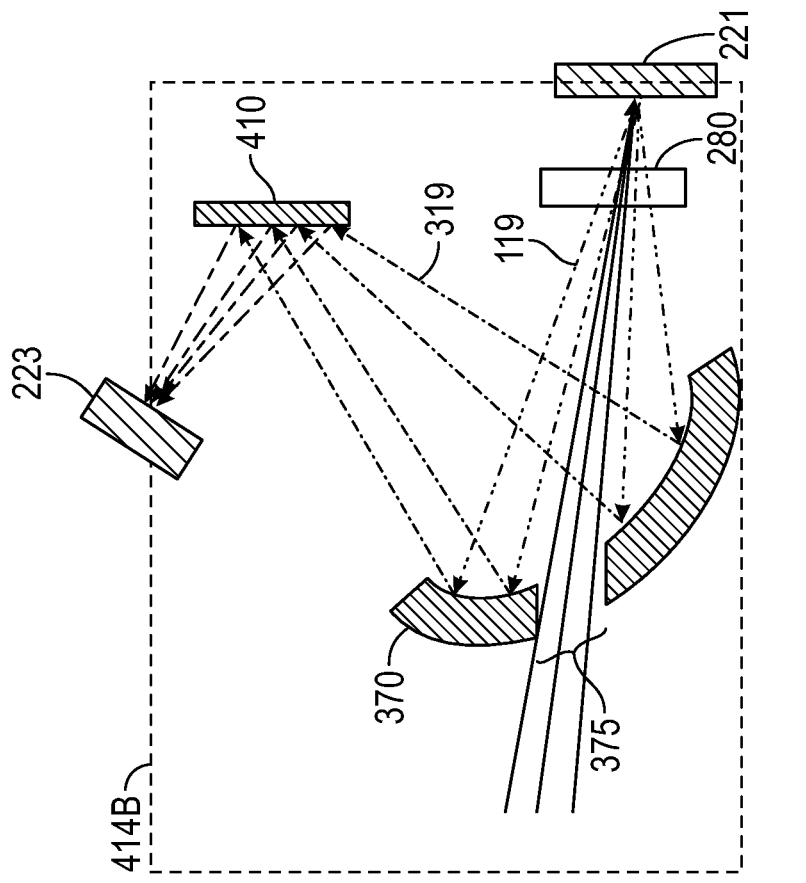
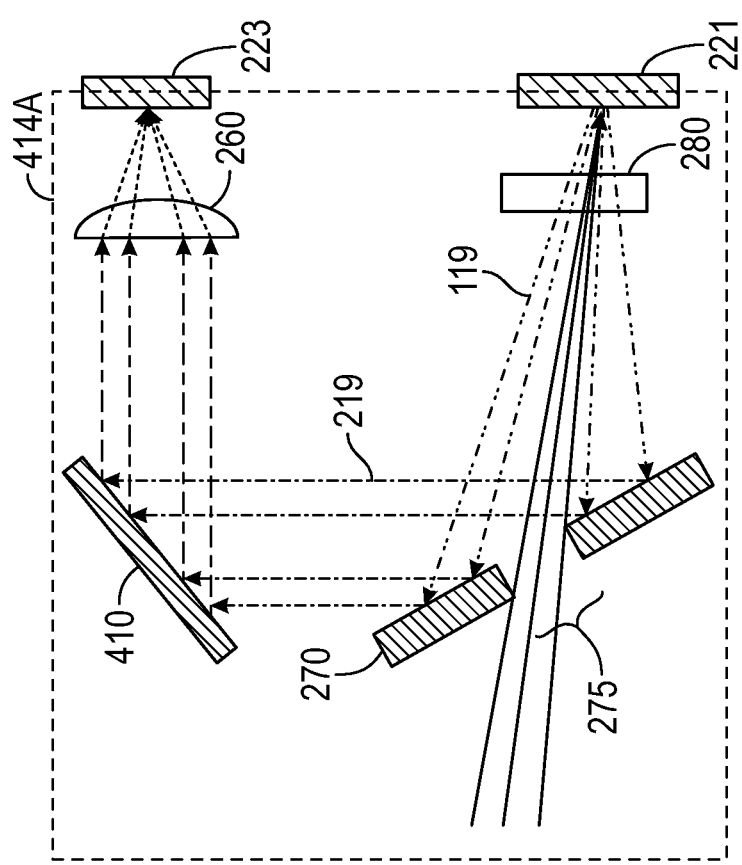
FIG. 4B
FIG. 4A

OPTICAL SPLITTER FOR LASER SURGICAL SYSTEMS WITH OVERHEATING PROTECTION

CLAIM OF PRIORITY

This application claims the benefit of priority under 35 U.S.C. § 119(e) of U.S. Provisional Patent Application Ser. No. 63/171,636, filed on Apr. 7, 2021, which is herein incorporated by reference in its entirety.

FIELD OF THE DISCLOSURE

The documents relates generally to optical surgical system, and more particularly to techniques for splitting an optical response signal that shares an optical pathway with an electrosurgical signal, and protecting optical components of the optical surgical system from overheating.

BACKGROUND

Laser or plasma systems have been used for delivering surgical laser energy to various target treatment areas such as soft or hard tissue. Examples of the laser therapy include ablation, coagulation, vaporization, fragmentation, etc. In lithotripsy applications, laser has been used to break down calculi structures in kidney, gallbladder, ureter, among other stone-forming regions, or to ablate large calculi into smaller fragments.

Endoscopes are typically used to provide access to an internal location of a subject such that a physician is provided with visual access. An endoscope is normally inserted into a patients body, delivers light to a target (e.g., a target anatomy or object) being examined, and collects signal (e.g., light) reflected from the object. The reflected signal carries information about the object being examined. Some endoscopes include a working channel through which the operator can perform suction or pass instruments such as brushes, biopsy needles or forceps, or perform minimally invasive surgery to remove unwanted tissue or foreign objects from the body of the patient.

SUMMARY

In certain conventional procedures employing electromagnetic energy, there is no way of identifying one or more characteristics (e.g., a type, a material, a composition, a composition profile, a structure or hardness) of an anatomical target while executing the procedure. For health-related procedures, it can be difficult to identify whether a target is soft or hard tissue in vivo. There are some surgical methods that can be used to extract tissue and then identify the composition or other characteristics of the tissue once it has been removed from the body. However, such characteristics cannot be determined in vivo.

Continuous identification of tissue characteristics during an endoscopic procedure can provide physicians with more information to better adapt their treatment method during the procedure. However, conventional tissue characterization techniques, which typically requires removal of tissue sample for analysis, cannot provide continuous monitoring and identification of tissue characteristics throughout a procedure.

Some endoscopic surgical systems can deliver laser energy to a target treatment area. Laser energy may be inadvertently dissipated in one or more optical components of the endoscopic surgical system, which may cause overheating and damage of such components. The present inventors have recognized, among other things, an unmet need for monitoring the temperature of optical components during an endoscopic surgery so as to prevent component overheating and damage.

This document provides improved systems, devices, and methods for continuous, in vivo monitoring and identification of tissue characteristics during a procedure. In one aspect of the present disclosure, techniques are provided for splitting an electrosurgical signal for use in an electrosurgery (such as ablation of a target) and an optical response signal that share a common optical pathway in a surgical system. An optical splitter comprises a first port to receive the optical response signal reflected from the target responsive to illumination incident, and a second port to receive the electrosurgical signal such as a laser beam from a laser system. The optical splitter comprises a reflector that can redirect the optical response signal to a spectroscopy system for analyzing a target characteristic. The reflector may have a guide member such as an aperture aligned to pass the electrosurgical signal therethrough and towards the target.

In another aspect of the present disclosure, a target identification system includes an optical splitter for splitting an electrosurgical signal (e.g., a laser beam) from an optical response signal such as reflected from an anatomical target in response to illumination thereof. The optical splitter includes a parabolic reflector with a concave reflective surface that can redirect the optical response signal to a spectroscopy system for analyzing target characteristics. Compared to reflectors of other shapes (e.g., a flat reflector), the parabolic reflector can more efficiently collect and converge an increased amount of optical response, achieve signal reflection and convergence without additional optical components, thereby reducing system complexity and potential alignment errors. Accordingly, overall system reliability can be improved.

In another aspect of the present disclosure, techniques are provided for determining a composition of a target in vivo (internal to a patient) such as while conducting a medical procedure at or near the target, such as an anatomical tissue target or a calculi target. As an example, for ablation of obstructive tissue such as renal calculi, composition information about the calculi can assist in executing the procedure more efficiently and effectively. A target identification system for use in electrosurgery can include a probe having an optical pathway to concurrently pass an electrosurgical signal such as a laser beam to the target, and an optical signal reflected from the target responsive to incident illumination. The system includes an optical splitter optically coupled to the probe. The optical splitter includes a reflector having an aperture aligned to pass the electrosurgical signal therethrough and towards a target, and a reflective surface to redirect the reflected optical signal to a spectroscopy system. The spectroscopy system can generate spectral information from the reflected optical signal, and identify the target as one with distinct composition. The spectral information can be used to adjust a setting of an electrosurgical energy system.

In yet another aspect of the present disclosure, techniques are provided for monitoring temperature of an optical component in an electrosurgical system, and protecting such optical component from overheating or damage. A temperature monitor can be coupled to one or more temperature sensors positioned at respective locations of the optical component, such as opposite surfaces of a reflector in an optical splitter. The temperature monitor can detect a temperature change during the electrosurgery from a baseline temperature, or a differential temperature such as between opposite surfaces of the reflector measured by respective temperature sensors. The temperature monitor can generate an overheating diagnostic, and adjust a setting of an electrosurgical energy system based on the overheating diagnostic. The temperature monitoring, overheating diagnostics, and overheating protection as described in accordance with various embodiments in this document can help prevent component damage and improve the reliability of the electrosurgical system.

Example 1 is a target identification system comprising: a probe including an optical pathway configured to pass (i) a first optical signal to an anatomical target and (ii) at least a portion of a second optical signal from the anatomical target responsive to illumination of the anatomical target; an optical splitter comprising: a first port coupled to the probe and configured to (i) direct the first optical signal to the optical pathway and (ii) receive the at least a portion of the second optical signal from the optical pathway; a second port configured to receive the first optical signal produced by a signal generator; and a parabolic reflector configured to redirect the at least a portion of the second optical signal; and a spectroscopy system configured to (i) receive the redirected at least a portion of the second optical signal, and (ii) based at least in part thereon, identify a characteristic of the anatomical target.

In Example 2, the subject matter of Example 1 optionally includes the parabolic reflector that can include a concave surface with reflective coating configured to reflect and converge the at least a portion of the second optical signal towards a third port of the optical splitter coupled to the spectroscopy system.

In Example 3, the subject matter of any one or more of Examples 1-2 optionally includes the parabolic reflector that can include a guide member configured to pass the first optical signal therethrough, the guide member including an aperture in the parabolic reflector spatially aligned with the first port.

In Example 4, the subject matter of any one or more of Examples 1-3 optionally includes second one or more reflectors positioned relative to the parabolic reflector and configured to collaboratively direct the at least a portion of the second optical signal towards a third port of the optical splitter coupled to the spectroscopy system.

In Example 5, the subject matter of any one or more of Examples 1-4 optionally includes the first optical signal that can include a laser beam emitted from a laser system optically coupled to the optical splitter via the second port.

In Example 6, the subject matter of Example 5 optionally includes a shield for preventing over-projection of the laser beam into the optical pathway.

In Example 7, the subject matter of any one or more of Examples 5-6 optionally includes at least one temperature sensor associated with the optical splitter for determining a temperature thereof in response to emission of the laser beam.

In Example 8, the subject matter of Example 7 optionally includes a controller circuit configured to generate a control signal to adjust a setting of the laser system based at least in part on the determined temperature.

In Example 9, the subject matter of any one or more of Examples 1-8 optionally includes the optical splitter that can further include one or more optical lenses configured to direct the first optical signal towards the first port.

In Example 10, the subject matter of Example 9 optionally includes the one or more optical lenses that can include at least one of a collimating lens, a focusing lens, or a biconvex lens.

In Example 11, the subject matter of any one or more of Examples 9-10 optionally includes the at least one of the one or more optical lenses that can include a reflective coating configured to redirect the at least a portion of the second optical signal to the spectroscopy system.

In Example 12, the subject matter of any one or more of Examples 1-11 optionally includes the spectroscopy system that can be configured to, based at least in part on the received at least a portion of the second optical signal, (i) generate a composition profile of the calculi target and (ii) identify a type of the calculi target.

In Example 13, the subject matter of any one or more of Examples 1-12 optionally includes the characteristic of the anatomical target that can comprise at least one of a type, a material, a composition, a composition profile, a structure or hardness of the anatomical target.

In Example 14, the subject matter of any one or more of Examples 1-13 optionally includes a controller circuit configured to generate a control signal to adjust a setting of the signal generator based on the received at least a portion of the second optical signal of the anatomical target.

Example 15 is an electrosurgical system, comprising: an electrosurgical energy system configured to generate an electrosurgical signal operable to ablate an anatomical target; a probe including an optical pathway configured to pass (i) the electrosurgical signal to the anatomical target and (ii) an optical signal from the anatomical target in response to illumination incident on the anatomical target; an optical splitter optically coupled to the probe, the optical splitter being configured to direct the electrosurgical signal to the optical pathway of the probe, and to receive at least a portion of the optical signal from the optical pathway of the probe and redirect the received at least a portion of the optical signal; and a temperature monitor coupled to at least one temperature sensor, the temperature monitor being configured to monitor a temperature of the optical splitter responsive to emission of the electrosurgical signal, and to generate an overheating diagnostic of the optical splitter based at least in part on the monitored temperature.

In Example 16, the subject matter of Example 15 optionally includes the optical splitter that can further comprise a reflector having an aperture configured to pass the electrosurgical signal therethrough, and the at least one temperature sensor is substantially proximate to the aperture.

In Example 17, the subject matter of any one or more of Examples 15-16 optionally includes the electrosurgical energy system that can include a laser system configured to emit laser pulses, and the temperature monitor is configured to synchronize temperature measurement with the laser pulses.

In Example 18, the subject matter of any one or more of Examples 15-17 optionally includes: (i) the optical splitter that can further comprise a reflector; (ii) the at least one temperature sensor includes a first temperature sensor on a non-reflective surface of the reflector; and (iii) the temperature monitor that can be configured to detect a temperature change of the non-reflective surface indicative of at least a portion of the optical signal being incident on the non-reflective surface of the reflector, and to generate the overheating diagnostic based at least in part on the detected temperature change of the non-reflective surface.

In Example 19, the subject matter of any one or more of Examples 15-18 optionally includes: (i) the optical splitter that can further comprise a reflector; (ii) the at least one temperature sensor includes a second temperature sensor on a reflective surface of the reflector; and (iii) the temperature monitor that can be configured to detect a temperature change of the reflective surface indicative of at least a portion of the optical signal reflected from the anatomical target and incident on the reflective surface of the reflector, and to generate the overheating diagnostic based at least in part on the detected temperature change of the reflective surface.

In Example 20, the subject matter of any one or more of Examples 15-19 optionally includes: (i) the optical splitter that can further comprise a reflector; (ii) the at least one temperature sensor that can include a first temperature sensor configured to sense a temperature of a non-reflective surface of the reflector opposite to a reflective surface, and a second temperature sensor configured to sense a temperature of the reflective surface; and (iii) the temperature monitor that can be configured to generate the overheating diagnostic based at least in part on a comparison between the temperature of the non-reflective surface and the temperature of the reflective surface.

In Example 21, the subject matter of Example 20 optionally includes the overheating diagnostic that can include: a first indicator of misalignment of the probe and the optical splitter if the temperature of the reflective surface is higher than the temperature of the non-reflective surface; and a second indicator of misalignment of the optical splitter and the electrosurgical energy system if the temperature of the non-reflective surface is higher than the temperature of the reflective surface.

In Example 22, the subject matter of any one or more of Examples 15-21 optionally includes a controller circuit configured to generate a control signal to adjust a setting of the electrosurgical energy system based at least in part on the monitored temperature.

Example 23 is a method for operating an electrosurgical system comprising an optical splitter and a probe coupled thereto, the method comprising: directing an electrosurgical signal to an anatomical target through the optical splitter the probe; receiving at least a portion of an optical signal reflected from the anatomical target in response to an illumination of the anatomical target; redirecting, via the optical splitter, the received at least a portion of the optical signal; monitoring a temperature of the optical splitter via a temperature sensor in response to emission of the electrosurgical signal; and upon determining that the monitored temperature exceeds a predetermined threshold, generating an overheating diagnostic of the optical splitter based at least in part on the monitored temperature.

In Example 24, the subject matter of Example 23 optionally includes the electrosurgical signal that can include laser pulses, and synchronizing the temperature monitoring with the laser pulses.

In Example 25, the subject matter of any one or more of Examples 23-24 optionally includes: monitoring the temperature of the optical splitter includes detecting a temperature change of a reflector in the optical splitter, the temperature change indicative of at least a portion of the optical signal being incident on the reflector; and generating the overheating diagnostic is based at least in part on the detected temperature change.

In Example 26, the subject matter of Example 25 optionally includes detecting the temperature change of the reflector that can include detecting a temperature change on at least one of a reflective surface or a non-reflective surface of the optical splitter.

In Example 27, the subject matter of any one or more of Examples 23-26 optionally includes monitoring the temperature of the optical splitter that can include detecting a first temperature of a non-reflective surface of a reflector in the optical splitter, and detecting a second temperature of a reflective surface of the reflector opposite to the non-reflective surface; and generating the overheating diagnostic based at least in part on a comparison between the first temperature and the second temperature.

In Example 28, the subject matter of Example 27 optionally includes the overheating diagnostic that can include: a first indicator of misalignment of the optical splitter and the probe, if the second temperature is higher than the first temperature; and a second indicator of misalignment of the optical splitter and an electrosurgical energy system generating the electrosurgical signal, if the first temperature is higher than the second temperature.

In Example 29, the subject matter of any one or more of Examples 23-28 optionally includes adjusting a setting of a electrosurgical energy system for generating the electrosurgical signal based at least in part on the monitored temperature.

The presented techniques are described in terms of health-related procedures, but are not so limited. This summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWING

FIGS. 4A-4B illustrate generally example optical splitters each including multiple reflectors that collaboratively redirect the optical response signal to an spectroscopy system.

DETAILED DESCRIPTION

Figure 1:
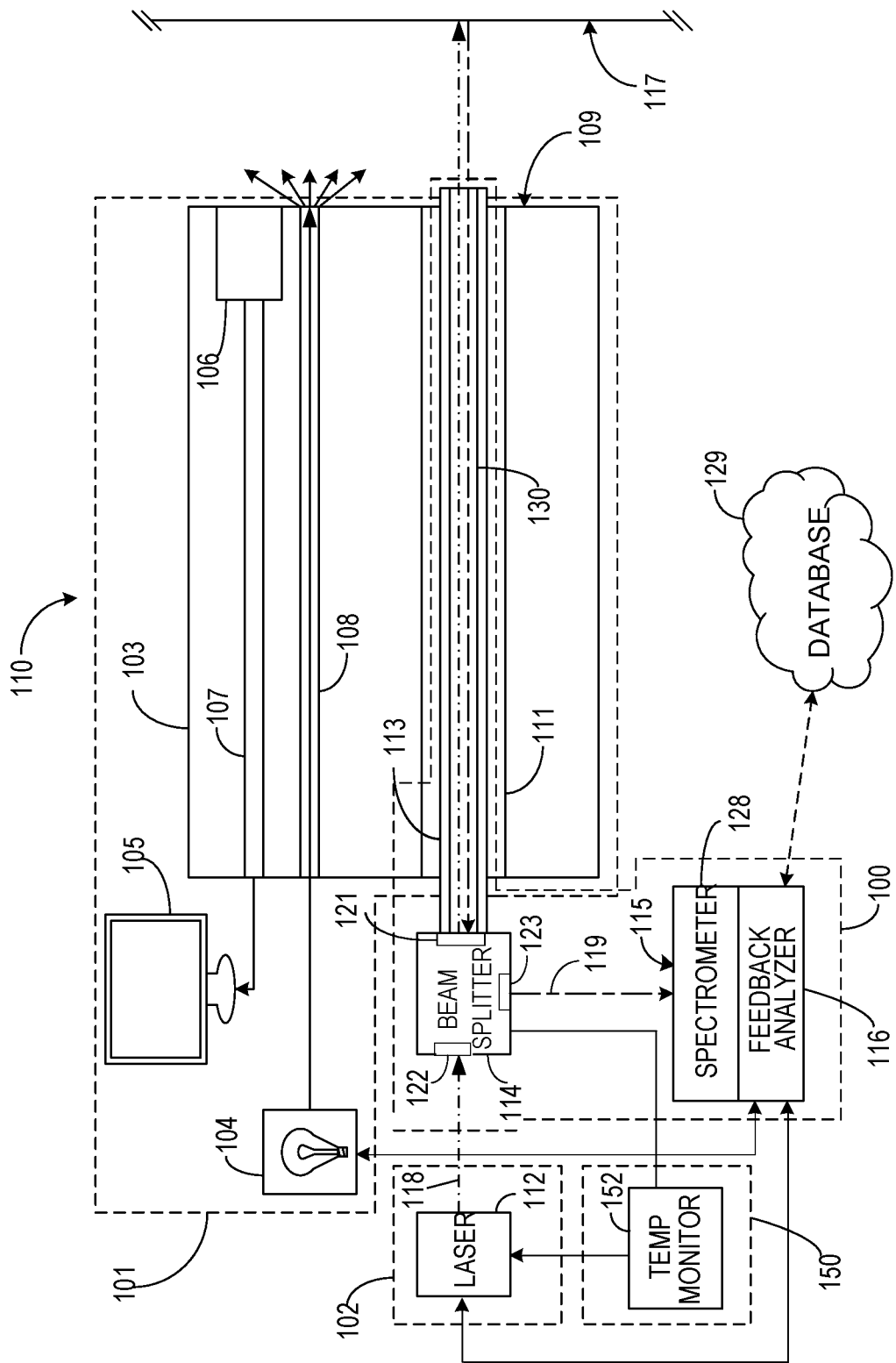
FIG. 1 illustrates generally an example target identification system within a surgical system such as an ablation system.

This document describes systems, devices, and methods for splitting an optical feedback signal reflected from a target in a patient's body from an electrosurgical signal, such as a laser beam generated by a laser system and directed to the target. The target can include an anatomical tissue target (e.g., soft tissue, hard tissue, or abnormal such as cancerous tissue), or a calculi target (e.g., kidney or pancreobiliary or gallbladder stone). The optical feedback signal and the electrosurgical signal are coupled with a common optical pathway. An optical splitter allows for reliable transmission of the electrosurgical signal with minimal attenuation, while at the same time directing the optical feedback signal to a spectroscopy system with minimal distortion. The spectroscopy system can continuously or recurrently identify one or more characteristics (e.g., a type, a material, a composition, a composition profile, a structure or hardness) of the target in vivo throughout the procedure. Feedback may be provided to the laser system to adjust laser output based on the spectral information and/or the identified target characteristic(s). This allows for instant adjustment of laser settings within a set range of the original laser setting selected by the user. According to some embodiments, the electrosurgical system can include an overheating protection system that can monitor temperature of an optical component such as the optical splitter, and adjust laser output to protect the optical component from overheating, thereby preventing damages to the optical splitter and the optical pathway. The systems and devices discussed herein may be used endoscopically or laproscopically.

Identifying the characteristic(s) (e.g., a type, a material, a composition, a composition profile, a structure or hardness) of tissue in vivo via an endoscope or laparoscope has numerous applications. For example, if the composition of a renal calculus is determined a priori, the treatment method may be based at least in part on the composition of the stone. For example, when using a laser to break-up or "dust" a stone, if it were known a priori that the stone had a hard composition, then the laser settings may be adjusted to settings that perform more effectively and/or efficiently on a hard kidney stone.

Also, techniques that require removal of a tissue sample to identify the composition cannot monitor the composition of the tissue on an ongoing basis through all or at least a portion of entire procedure. The present techniques can allow measurement and analysis of the characteristic(s) (e.g., a type, a material, a composition, a composition profile, a structure or hardness) of an anatomical target or a calculi target at the tip of the endoscope or laparoscope. These techniques can provide more information during a health related procedure, such as a surgical or diagnostic procedure, to better adapt a treatment method during the procedure. For example, if a procedure involves breaking a renal calculus into tiny pieces, e.g., "dusting" the renal calculi, and the renal calculus has a hard surface, but a soft core, the continuous or other ongoing monitoring of target composition via the endoscope or laparoscope can allow adjustment of, for example, a setting of the instrument doing the "dusting" during the procedure, such as laser settings for a laser ablation instrument. The identification of the target can allow for first providing settings that perform better (e.g., more effectively and/or efficiently) on the hard surface of the stone to then providing settings that perform better on the soft core of the stone.

FIG. 1 illustrates generally an example target identification system 100 within a surgical system 110, such as an electrosurgical system that uses laser energy to ablate a target 117 in a patient's body. The target 117 can include an anatomical tissue target (e.g., soft tissue, hard tissue, or abnormal such as cancerous tissue), or a calculi target (e.g., kidney or pancreobiliary or gallbladder stone). The surgical system 110 can include visualization equipment such as an endoscope 101, the target identification system 100, primary medical instrument such as a surgical laser system 102, and an overheating protection system 150. The endoscope 101 can include an endoscope probe 103, a light source 104 and a display 105. The endoscope probe 103 can include a camera 106, one or more optical signal communication pathways 107, 108, and at least one working lumen 111. A distal portion of the endoscope probe 103 can be inserted within a patient's body. The light source 104, one or more optical pathways 107, 108, and display 105 can allow an end-user, such as a physician or surgeon or robotic device, to illuminate and observe an internal area of the patient's body at or near the distal end 109 of the endoscope probe 103. The light source 104 can emit electromagnetic radiation (e.g., visible light, infrared light, ultraviolet light, or fluorescent light) to illuminate the area at or beyond the distal end 109 of the endoscope probe 103 via a first optical pathway 108. Alternatively, the light source 104 may include an illumination light, such as one or more LEDs of a visualization system, positioned at a distal end of an endoscope and configured to illuminate the area proximate to the target 117. In an example, the second optical pathway 107 can communicate image signal information from the camera 106 at the distal end 109 of the endoscope probe 103 to signal processing circuitry at the display 105 for displaying an image of the area at or beyond the distal end 109 of the endoscope probe 103, such as an image of the target 117. In some examples, the second optical pathway 107 can include one or more components such as one or more optical fibers, and the display 105 can include an eyepiece for the end-user to observe the area at or beyond the distal end 109 of the endoscope probe 103. In certain examples, the second optical pathway 107 can couple viewing image signal information from the camera 106 to the display 105 such as for the end-user to observe the area at or beyond the distal end 109 of the endoscope probe 103. In some examples, the camera 106 can be located at or near the proximal end of the endoscope probe 103, such as near the display 105, and one or more optical fibers can form the second optical pathway 107 to transmit the image information from the distal end 109 of the endoscope probe 103 to the camera 106. In some examples, the camera 106 can be located at the distal end 109 of the endoscope probe 103, and image information can be transmitted to the display 105 via electrical conductors forming at least a portion of the second optical pathway 107 integrated with the endoscope probe 103.

The working lumen 111 can further allow the end-user to insert and extract a portion of the primary medical instrument (such as one or more surgical tools) for operating about the targeted internal region of the patient's body being visualized using the endoscope probe 103. For example, for the surgical laser system 102, the primary medical instrument can include a working probe 113 and a laser generator 112 to allow ablation of target tissue or a calculi target at or near the distal end 109 of the endoscope probe 103. In such a system, for either endoscopic or laparoscopic procedures, a laser beam 118 can pass laser energy through the working lumen 111 to treat hard and soft tissue. In certain examples, the surgical laser system 102 can produce the laser beam 118 in a wide wavelength range from ultraviolet (UV) to infrared (IR) (e.g., 200 nm to 10000 nm). Some lasers can produce an output in a wavelength range that can be highly absorbed by soft or hard tissue, for example 1900-3000 nm for water absorption or 400-520 nm for oxy-hemoglobin and/or deoxy-hemoglobin absorption.

The target identification system 100 can include an optical splitter 114 (also referred to as a beam splitter) and a spectroscopy system 115. In some examples, the working probe 113 may be a part of the target identification system 100. The beam splitter 114 can include (i) a first port 121 for a common optical pathway 130 that can concurrently transmit the laser beam 118 and an optical response signal 119 such as reflected or radiated from the target 117, (ii) a second port 122 for an optical pathway coupled to the surgical laser system 102, and (iii) a third port 123 for a feedback optical pathway coupled to the spectroscopy system 115. The spectroscopy system 115 can include a spectrometer 128 and an optional feedback analyzer 116. In an example, the target identification system 100 can use information of the optical response signal 119 to assist in determining one or more characteristics (e.g., a material or a composition) of the target 117. The optical response signal 119 can include, for example, light visible to the human eye, florescent emissions, ultra-violet light, infrared light, or combinations thereof.

In certain examples, information of the optical response signal 119 can be used to more efficiently execute a procedure. In an example, electromagnetic radiation from the light source 104 incident on the target can be reflected off of the target 117 within the internal area of the patient's body at or near the distal end 109 of the endoscope probe 103, or can cause the target 117 to emit optical information, such as by florescence, for example. Optical information conveyed via the optical response signal 119 is also referred to as image response information or optical response information herein. The spectrometer 128 can be optically coupled to the beam splitter 114, and provide spectral measurements from the optical response signal 119. Examples of the spectrometer 128 may include a Fourier Transform Infrared (FTIR) spectrometer, a Raman spectrometer, a UV-VIS spectrometer, a UV-VIS-IR spectrometer, or a fluorescent spectrometer, among others.

Spectroscopy/spectrometry techniques can be used to identify the characteristic(s) (e.g., a type, a material, a composition, a composition profile, a structure or hardness) via the spectrum reflected, transmitted, emitted, absorbed, or not absorbed by a target surface. Optical spectroscopy can provide timely analysis of organic and inorganic materials. For ablation, optical spectroscopy can help provide several advantages, such as including, but not limited to, integration with fiber laser ablation techniques, nondestructive methods of material chemical composition analyses, real-time or near real-time composition estimates or composition profiles, and applicability for analyses of different types of biological materials: hard and soft tissue, stones, and others. Spectroscopic techniques can be used alone or in combination to analyze hard or soft tissue chemical composition, and generate digital spectral data. Examples of the digital spectral data may include one or more characteristic spectral features extracted from a reference spectrum. Examples of the characteristic reflectance features may include reflectance intensity (or normalized reflectance spectral intensity) at a specific wavelength or over a wavelength range, a statistical value calculated from the reflectance spectrum (e.g., a variation of reflectance over two or more different wavelengths, a rate of change of reflectance over a range of wavelengths, or the like), or a graphical feature representing the morphology of at least a portion of the spectral reflectance curve (e.g., a slope, a curvature, a segment of the curve, or the like). In some examples, one or more types of spectroscopy, including but not limited to, color, ultra-violet, deep ultra-violet, visual light, near-infrared, and florescent spectroscopy, can be used with the endoscope 101 to identify the composition of the target 117. In an example, the spectroscopy system 115 can (i) initiate and control the light source 104 to illuminate the target 117 via, for example, the first optical pathway 108 of the endoscope probe 103, (ii) receive optical response signal 119 reflected or radiated from the target 117 such as via an optical pathway of the working probe 113 (such as the common optical pathway 130), and (iii) generate spectral data based on the optical response signal 119.

The feedback analyzer 116 can determine, from the spectral measurement generated by the spectrometer 128, characteristic(s) of the target 117, such as a type, a material, a composition, a composition profile, a structure or hardness, based on the spectral measurements. In an example, the feedback analyzer 116 can estimate a compositions profile of the materials represented by the spectral data, and can display such estimates. The composition or structure information can be useful to help provide feedback that can be used for more efficiently performing the surgical procedure. For example, the feedback analyzer 116 can compare the spectroscopic response signal with an available database library of tissue composition data. The feedback analyzer 116 can identify target material composition based on the spectroscopic response signal and suggest a configuration for the surgical laser system 102 to achieve effective tissue treatment for the identified tissue composition. In an example, the feedback analyzer 116 can identify a calculi target as one of a plurality of calculi types with distinct compositions, such as tones or stone fragments in various stone-forming regions such as urinary system, gallbladder, nasal passages, gastrointestinal tract, stomach, or tonsils. In an example, the calculi target may be identified as one of stone types with distinct chemical compositions, such as one of a calcium phosphate (CaP) stone, a magnesium ammonium phosphate (MAP) stone, a monohydrate calcium oxalate (COM) stone, a cholesterol-based stone; a dihydrate calcium oxalate (COD) stone, a cystine stone, or a uric acid (UA) stone. In another example, the feedback analyzer 116 can identify an anatomical tissue target as one of a plurality of tissue types, such as soft tissue (e.g., muscles, tendons, ligaments, blood vessels, fascia, skin, fat, and fibrous tissues), hard tissue such as bone, connective tissue such as cartilage, among others. In some example, the anatomical tissue target may be identified as one of tissue types with distinct anatomical locations. For example, a renal tissue target may be identified as one of calyx tissue, cortex tissue, medulla tissue, or ureter tissue. In another example, an identified tissue target may be identified as normal tissue or abnormal tissue (e.g., cancerous tissue). In yet another example, an identified tissue target may be identified as treatment area (e.g., tumor or polyp intended for removal) or a non-treatment area (e.g., blood vessels, muscle, etc.).

In certain examples, the feedback analyzer 116 can provide one or more control signals or control data to adjust a setting of the surgical laser system 102. In a laser ablation example, the feedback analyzer 116 or an intermediate device, can include control circuitry to program or adjust laser settings automatically based on the target characteristic(s) (e.g., a type, a material, a composition, a composition profile, a structure or hardness). Examples of adjusting the laser settings may include delivering or withhold delivering the laser beam, or adjust a laser beam parameter such as wavelength, power, power density, energy, or a pulse parameter (e.g., pulse width, pulse rate, amplitude, duty cycle, pulse shape), exposure time, total dose or energy, or one or more combinations thereof, among others. In some examples, adjustment of the laser settings can be limited or constrained to be within a set individual or multivariate safe operating range such as based on a setting selected by the end-user at the start of the procedure.

In certain examples, the spectroscopy system 115 can optionally communicate with a database 129. In some examples, the database 129 can be a repository for storing measurements and other information associated with a procedure. In some examples, as the database collects more information, the spectroscopy system 115 or a portion thereof, such as the feedback analyzer 116, can interact with information of the database 129 to determine, for example, the most efficient application of the laser system 102 based on spectroscopic information collected or analyzed during the procedure and/or compared with the historical information available in the database 129. In certain examples, the database may be able to provide temporal recipe (e.g., such as laser pulse parameter values and/or temporal variations thereof) for configuring the surgical laser system 102 as the spectroscopic information of a procedure is collected and analyzed. In certain examples, the database 129 can include an internet-based or a cloud-based database and may include applications designed for interacting with a feedback analyzer 116 or some other portion of the spectroscopy system 115 to assist in executing an efficient surgical procedure based on historical procedure information and/or adaptive to the specific spectroscopic information collected during the procedure.

For example, for a laser ablation system, the laser settings that can be part of a recipe for configuration of the surgical laser system 102 can include, but are not limited to, laser operation mode (e.g., pulse or continuous wave), power, energy, frequency, pulse shape, pulse profile, or one or more combinations thereof. In certain examples, the surgical laser system 102 can operate in an automatic mode or a semi-automatic mode among other modes. In the automatic mode, the laser settings can be automatically controlled based on the estimated target characteristic(s) (e.g., a type, a material, a composition, a composition profile, a structure or hardness). In the semi-automatic mode, the laser settings can be adjusted based on the estimated target characteristic(s) after receiving some confirmatory indication of an operator's approval for making the setting change. The combination of the surgical laser system 102, spectroscopy system 115, and the feedback analyzer 116 can be used in an ongoing intraoperative feedback mode such as to continuously or recurrently identify the characteristic(s) (e.g., a type, a material, a composition, a composition profile, a structure or hardness) of target 117 through the working probe 113 and update the laser settings during or throughout a procedure. It is understood that other surgical techniques besides laser-based surgical techniques as discussed herein are possible to use with the target identification system 100 without departing from the scope of the present subject matter In certain examples, a single optical pathway of the working probe 113 of the target identification system 100 can be used to transport a first optical signal (such as the laser beam 118) to or from the target 117 at the distal end 109 of the working probe 113 and can also be used to transport a second optical signal (such as the optical response signal 119) from the distal end 109 of the working probe 113 to the spectroscopy system 115. The beam splitter 114 can merge multiple optical pathways into a single optical pathway or to separate optical information from a common optical pathway (such as the optical pathway 130) to one or more separate optical pathways. The beam splitter 114 can include a reflector having a guide member, such as an aperture extending between two opposite surfaces of the reflector. The guide member or the aperture can be aligned to pass the laser beam 118 therethrough, and direct the laser beam 118 towards the target 117 via the common optical pathway 130. The guide member can advantageously avoid or substantially reduce attenuation or distortion of the laser energy before entering the optical pathway 130. The reflector has a reflective surface positioned to face the first port 121 and redirect the incoming optical response signal 119, transmitted through the optical pathway 130, towards the spectroscopy system 115 through the third port 123. In some examples, the reflective surface includes a wavelength sensitive coating such an anti-reflective coating or material or a dichroic coating or material or a combination thereof. Suitable material for anti-reflection coatings can include $SiO_2$ (refractive index between about 1.4 and about 1.5), SiO (refractive index between about 1.8 and about 1.9), $Si_3N_4$ (refractive index of about 1.9), $TiO_2$ (refractive index of about 2.3), $Ta_2O_5$ (refractive index between about 2.1 and about 2.3), $MgF_2$ (refractive index between about 1.4 and about 1.5), $BaF_2$ (refractive index of about 1.47), $CaF_2$ (refractive index of about 1.39), and others. Examples of the beam splitters with a hollow reflector are discussed below, such as with reference to FIGS. 2A-2B and 3A-3B. Although the beam splitter 114 is shown in FIG. 1 as a part of the target identification system 100, its application is not limited. The beam splitter 114, or a variant thereof such as discussed below with reference to FIGS. 2A-2B, 3A-3B and 4A-4B, can be used in other optical systems or electrosurgical systems.

The overheating protection system 150 can protect optical components of the surgical system 110, such as the beam splitter 114 or a part thereof, from overheating. Heat accumulation may be caused by a portion of the laser beam 118 dissipating in the optical components as it passes through the beam splitter 114. Additionally or alternatively, in some instances, a portion of the laser energy incident on the target 117 may get reflected or radiated back to the endoscope probe 103, travel through the common optical pathway 130, and scatter onto the surface of an optical component such as the beam splitter 114, causing a temperature increase therein. The overheating protection system 150 can include a temperature monitor 152 electrically coupled to one or more temperature sensors to measure temperature of the beam splitter 114 or other optical components. In an example, the overheating protection system 150 may include controller circuitry, such as included in the temperature monitor 152, that can generate a control signal to the surgical laser system 102 to adjust a setting of the laser generator 112 based on the monitored temperature. For example, in response to an increased temperature of the beam splitter 114 exceeding a threshold, the controller circuit may shut down the laser generator 112 temporarily, or change one or more laser beam parameters to reduce the laser energy output. In some examples, the temperature monitor 152 may monitor respective temperatures of different optical components, or respective temperatures at different locations of an optical component. Based on the temperature measurements, the temperature monitor 152 may identify a cause of overheating, such as either due to the laser beam 118 dissipating in the beam splitter 114, or due to reflected laser energy scattering onto the beam splitter 114. The temperature monitor 152 may further generate a diagnostic generate a diagnostic of optical component overheating. Examples of the temperature monitor and overheating protection system are discussed below, such as with reference to FIGS. 2A-2B and 3A-3B.

Figure 2A:
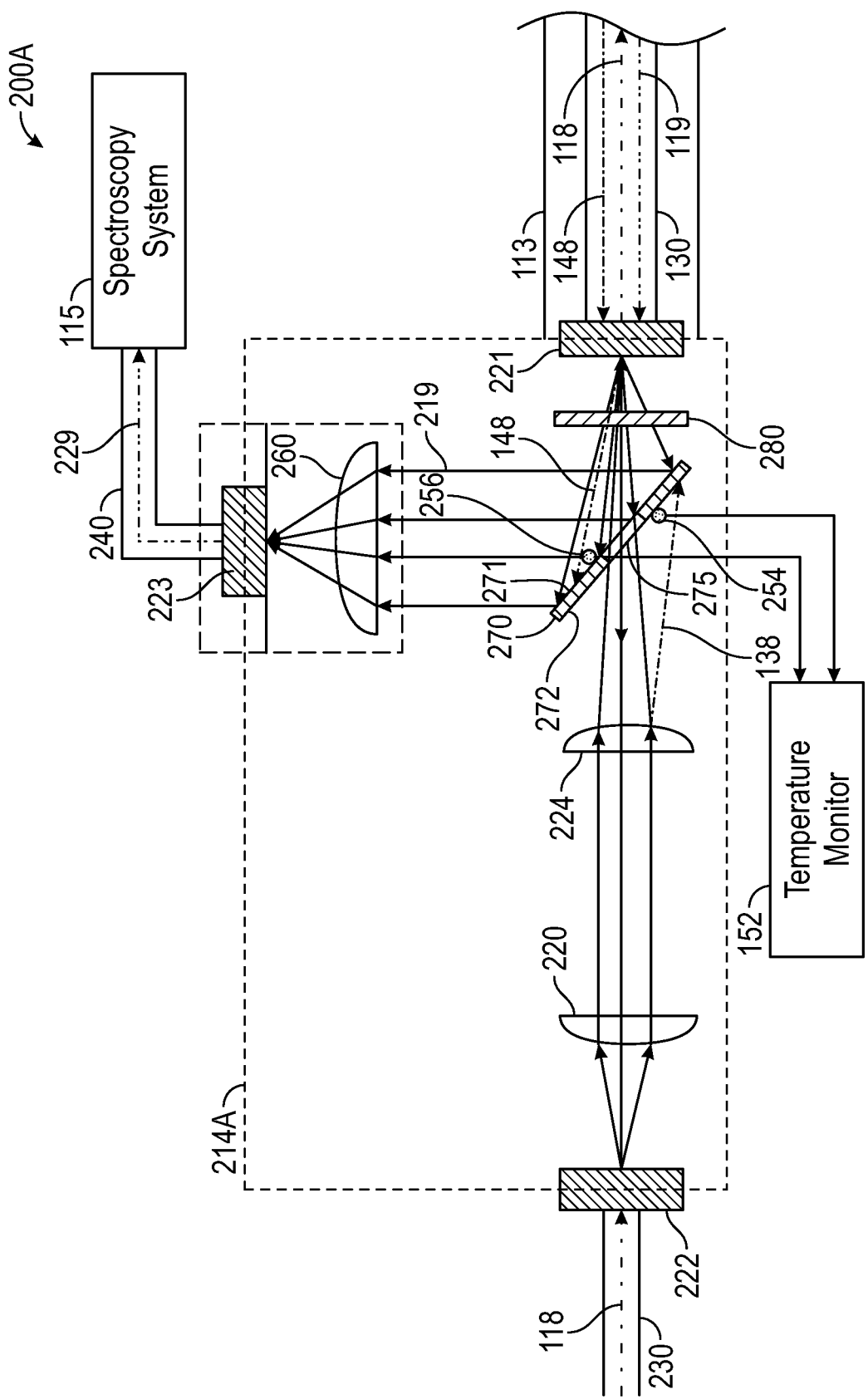
FIGS. 2A-2B illustrate generally example target identification systems each including an optical splitter that comprises a flat hollow reflector.
Figure 2B:
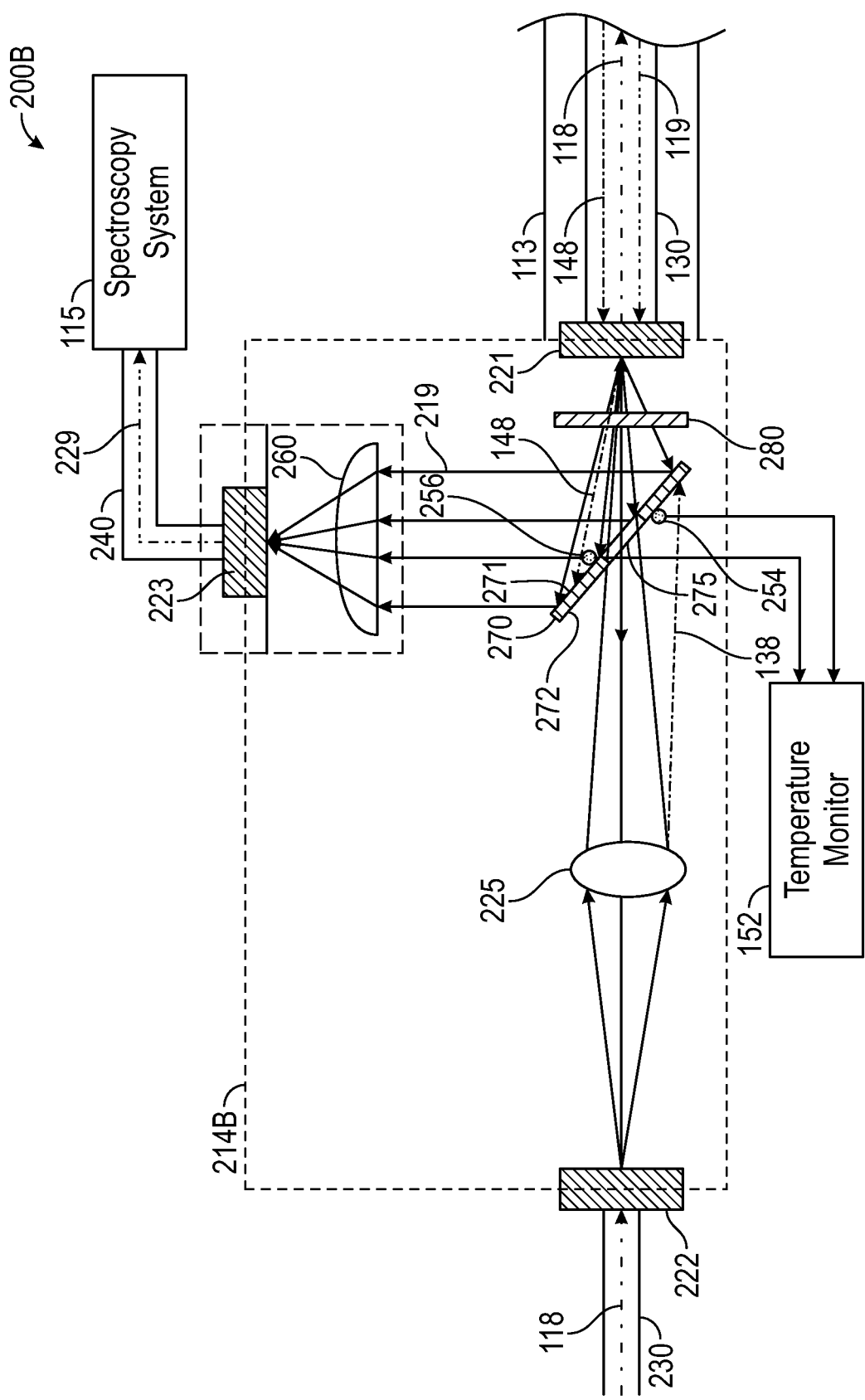

FIGS. 2A-2B illustrate generally example target identification systems each including a beam splitter that comprises a flat hollow reflector. A target identification system 200A, as illustrated in FIG. 2A, is an example of the target identification system 100, and includes a beam splitter 214A, a probe 113, and a spectroscopy system 115. The beam splitter 214A can include one or more ports 221, 222, and 223, a collimating lens 220, a focusing lens 224, and a hollow reflector 270. Similar to the ports 121, 122, and 123 of the beam splitter 114, the first port 221 can receive the common optical pathway 130, such as a surgical fiber in an endoscope, that can concurrently transmit the laser beam 118 towards the target 117 and transmit the optical response signal 119 reflected or radiated from the target 117 back to beam splitter 214A. The second port 222 can receive a second optical way, such as a laser fiber 230, coupled to the surgical laser system 102. The third port 223 can receive a third optical pathway, such as a spectrometer fiber 240, coupled to the spectroscopy system 115. As illustrated in FIG. 2A, the laser beam 118 can be directed from the second port 222 to the first port 221 via the collimating lens 220, the focusing lens 224, and the hollow reflector 270. The hollow reflector 270 can be made of metal, glass, or plastic, among other materials. In an example, the hollow reflector 270 is a hollow mirror. The hollow reflector 270 has a reflective surface 271 (also referred to as a "front surface") facing the first port 221 and the common optical pathway 130, and a non-reflective surface 272 (also referred to as a "back surface") opposite to the reflective surface 271 and facing the second port 222 and the collimating lens 220 and the focusing lens 224. The hollow reflector 270 can have an aperture 275, such as a through-hole extending from the front surface to the back surface of the reflector body. The aperture 275 may be located at substantially the center of the hollow reflector 270. Alternatively, the aperture 275 may be located at other locations of the reflector body away from the center. The aperture 275 can have specific size and shape, and can be aligned with the path of the collimated and focused laser beam 118 to substantially pass the laser beam therethrough without obstruction. In some examples, the reflective surface 271 may include a wavelength sensitive material or coating, such as an AR material, that can be transparent or anti-reflective to the wavelength of the laser, but highly reflective to wavelengths of interest of the optical response signal 119. As such, much if not all of the laser energy can be passed from the second port 222 to the first port 221. In some examples, the focusing lens 224 may likewise include, on its surface facing the hollows reflector 270, a wavelength sensitive material or coating transparent or anti-reflective to the wavelength of the laser but highly reflective to wavelengths of the optical response signal 119, such that the laser energy can be passed through without obstruction, while a portion (if any) of the optical response signal 119 leaking through the aperture 275 of the hollow reflector 270 can be redirected to the third port 223. The collimating lens 220, the focusing lens 224, and the aperture 275 can be spatially aligned with the first port 221, such that the laser beam 118 can be directed to the optical pathway 130 via the first port 221.

Among other advantages, the aperture 275 can effectively avoid or reduce attenuation or distortion of the laser beam as it passes through the beam splitter 214A before entering the common optical pathway 130. Additionally, as the aperture 275 is open to the laser beam 118, the reflector body is less likely to interact directly with the laser beam 118 and absorb laser energy. Accordingly, chances of heat buildup and damages to the reflector body or other optical components of the beam splitter 214A can be reduced, system safety and reliability can be improved.

Although only one aperture 275 is shown in the hollow reflector 270, this is by way of example and not limitation. In some examples, the hollow reflector 270 may include two or more apertures spatially apart from each other to pass respective optical signals. In an example, two separate laser beams may be transmitted through respective laser fibers and enter the beam splitter 214A via the second port 222. A first laser beam has an energy level or a laser setting for ablating or dusting a hard stone or a hard portion of a calculi target with a first composition, and a second laser beam has a different energy level or a different laser setting for ablating or dusting a soft stone or a soft portion of the calculi target having a different second composition. The two laser beams can be collimated and focused by the lens 220 and 224, and directed through respective apertures on the reflector body towards the common optical pathway 130.

In the example as illustrated in FIG. 2A, the hollow reflector 270 is a flat reflector (e.g., a flat mirror) comprising a flat reflective surface 271 and a flat nonreflective surface 272. The optical response signal 119, reflected or radiated from the target 117 and directed to the beam splitter 214A through the common optical pathway 130, can be coupled from the first port 221 to the third port 223 via the hollow reflector 270. The flat reflective surface 271 can be positioned to reflect the optical response signal 119, and redirect the reflected optical response signal 219 towards the third port 223 of the beam splitter 214A. In an example, the beam splitter 214A may include a focusing lens 260 to converge the reflected optical response signal 219 towards the third port 223. The converged optical response signal 229 can travel to the spectroscopy system 115 via the spectrometer fiber 240.

As the laser beam passes through an optical instrument such as a beam splitter, certain optical components may absorb laser energy and become overheated. As discussed above, the aperture 275 allows majority (e.g., 90% or, in some embodiments, 80% or 70%) of the laser beam to pass therethrough without interacting directly with the reflector 270, which can substantially reduce the chance of heat buildup on the reflector body. However, in certain occasions, some laser energy 138 may dissipate in optical components such as the hollow reflector 270, which may lead to temperature increase. This may occur, for example, due to coupling anomaly between the laser system 102 and the beam splitter 214A, a misalignment of the laser fiber 230 and the lens system in the beam splitter 214A, or defects of the lens system such as crack, dust, or degradation of the collimating lens 220 or the focusing lens 224. The dissipating laser energy 138 thus may heat the non-reflective surface (back surface) of the hollow reflector. Additionally or alternatively, in some instances, a portion of the laser beam directed to the target 117 may be reflected or radiated back to the endoscope probe. The reflected laser beam 148 can travel back through the common optical pathway 130, and scatter onto, and heat, the reflective surface (front surface) of the hollow reflector 270.

The target identification system 200A can include a temperature monitor 152 to monitor temperature of the hollow reflector 270 or a portion thereof. The temperature monitor 152 can be electrically coupled to one or more temperature sensors to detect a temperature change in the hollow reflector 270 responsive to issuance of laser beam 118. The temperature sensors can be contact sensors, or non-contact sensors. Examples of the temperature sensors include thermocouple, thermistor, infrared sensor, bi-metallic element, resistance temperature detector, fluorescent temperature sensor, temperature-sensitive or temperature-dependent luminescent materials, among others. In some examples, the temperature monitor 152 can synchronize sampling of the temperature measurement with the laser pulses. For example, the temperature monitor 152 may sample the temperature measurement at a sampling rate substantially equal to the laser pulse rate, such that temperature data is sampled immediately after issuance of every laser pulse. Alternatively, the temperature monitor 152 may sample the temperature measurement at integer multiples of the laser pulse rate, such that the temperature measurement is sampled immediately after issuance of every N (>2) laser pulses. Because the time of laser pulse firing is approximately the time of the dissipating laser energy 138 incident on and heating the reflector body and thereby causing a high temperature gradient on the body surface of the reflector, synchronizing the temperature measurement with laser pulses can help improve the sensitivity and accuracy of detecting a temperature change in the hollow reflector 270.

By way of example and not limitation, and as illustrated in FIG. 2A, the temperature monitor 152 can be electrically coupled to one or more of a first temperature sensor 254 and a second temperature sensor 256 each located on the body of the hollow reflector 270. In an example, the temperature sensor 252 and/or the temperature sensor 254 may be substantially proximate to the aperture 275. As described above, the aperture 275 can be positioned in alignment with the collimated and focused laser beam. However, slight misalignment of the laser fiber 230 with respect to the beam splitter 214A, or certain defects of the collimating lens 220 and/or the focusing lens 224, may more likely cause laser energy to dissipate in the vicinity the aperture 275 than other parts of the reflector body far away from the aperture 275. Accordingly, if the misalignment occurs, temperature of the areas close to the aperture 275 is likely higher than other areas of the reflector surface. Positioning the temperature sensors at locations in close proximity to the aperture 275 may improve the sensitivity and accuracy of detecting reflector overheating such as due to laser fiber misalignment or defects of the lens system.

The first temperature sensor 254 can be positioned on the non-reflective surface 272 of the hollow reflector 270. The first temperature sensor 254 can sense a temperature ($T_N(1)$) of a portion of the non-reflective surface 272 during the issuance of laser energy, and a baseline temperature ($T_N(0)$) of the non-reflective surface 272 such as prior to the issuance of laser energy. The temperature monitor 152 can detect a temperature change ($\Delta T_N$) at the non-reflective surface 272 from the baseline temperature to the temperature during laser firing, that is, $\Delta T_N = T_N(1) - T_N(0)$. If the temperature increase $\Delta T_N$ satisfies a specific condition such as exceeding a threshold value ($T_{N-th}$), i.e., $\Delta T_N > T_{N-th}$, the temperature monitor 152 may determine that the temperate rise is substantial, and that laser energy 138 dissipating in the non-reflective surface 272 has caused the hollow reflector 270 to be overheated.

The second temperature sensor 256 can be positioned on the reflective surface 271. The second temperature sensor 256 can sense a temperature ($T_R(1)$) of a portion of the reflective surface 271 during the issuance of laser energy, and a baseline temperature ($T_R(0)$) of the reflective surface 271 such as prior to the issuance of laser energy. The temperature monitor 152 can detect a temperature change ($\Delta T_R$) at the reflective surface 271 from the baseline temperature to the temperature during laser firing, that is, $\Delta T_R = T_R(1) - T_R(0)$. If the temperature increase $\Delta T_R$ satisfies a specific condition such as exceeding a threshold value ($T_{R-th}$), i.e., $\Delta T_R > T_{R-th}$, the temperature monitor 152 may determine that the temperate rise is substantial, and that the reflected laser beam 148 scattering onto the reflective surface 271 has caused the hollow reflector 270 to be overheated.

The temperature monitor 152 may generate an alert or a notification of reflector overheating, and present it to a user such as via the display 105. The temperature monitor 152 may additionally or alternatively generate a diagnostic of overheating indicating probable cause of heating. For example, if $\Delta T_N > T_{N-th}$, an overheating diagnostic of coupling anomaly between the laser system 102 and the beam splitter 214A, a misalignment of the laser fiber 230 and the lens system in the beam splitter 214A, or defects of the lens system such as crack, dust, or degradation of the collimating lens 220 or the focusing lens 224, may be generated. If $\Delta T_R > T_{R-th}$, an overheating diagnostic of a misalignment of the common optical pathway 130 (e.g., a surgical fiber) or the probe 113 and the beam splitter 214A may be generated. The diagnostic information may be presented to a user, such as via the display 105. In some examples, in response to a diagnostic of misalignment, a recommendation for corrective actions (e.g., adjusting alignment, or replacing a part such as the endoscope probe) may be provided to the user, such as via the display 105.

In some examples, the temperature monitor 152 may detect overheating of optical components such as the reflector 270 and generate a diagnostic of overheating based on differential temperature between the reflective surface 271 and the non-reflective surface 272 during the issuance of laser energy. For example, the temperature monitor 152 may compare the temperature ($T_N(1)$) of the non-reflective surface 272 sensed by the first temperature sensor 254, to the temperature ($T_R(1)$) of the reflective surface 271 sensed by the second temperature sensor 256, and generate an overheating diagnostic based on the comparison. In an example, the temperature monitor 152 can trend the differential temperature $T_N(1) - T_R(1)$ over time. If the temperature of the non-reflective surface $T_N(1)$ is higher than the temperature of the reflective surface $T_R(1)$ by at least a specified margin, an indicator of coupling anomaly between the laser system 102 and the beam splitter 214A, a misalignment of the laser fiber 230 and the lens system in the beam splitter 214A, or defects of the lens system such as crack, dust, or degradation of the collimating lens 220 or the focusing lens 224, may be generated. If the temperature of the reflective surface $T_R(1)$ is higher than the temperature of the non-reflective surface $T_N(1)$ by a specified margin, an indicator of misalignment of the common optical pathway 130 (or the probe 113) and the beam splitter 214A may be generated.

In some examples, the temperature monitor 152 may generate and present to the user recommendations for remedial actions based on the overheating diagnostics. For example, if overheating is detected based on $\Delta T_R > T_{R-th}$, or the differential temperature $T_R(1) - T_N(1)$ exceeding a specific margin, then a recommendation to realign the probe 113 or the surgical fiber with the beam splitter, or replace the surgical fiber, may be presented to the user. If overheating is detected based on $\Delta T_N > T_{N-th}$, or the differential temperature $T_N(1) - T_R(1)$ exceeding a specific margin, then a recommendation to replace or repair the beam splitter may be presented to the user. In some examples, as described above with reference to FIG. 1, in response to the detected optical component overheating, the overheating protection system 150 can automatically adjust a setting of the laser system, such as shutting down the laser generator 112 temporarily, or change one or more laser beam parameters to reduce laser energy emission.

The beam splitter 214A can include a blast shield 280 proximate to the first port 221. The blast shield 280 can prevent the transmitting laser beam from over-projecting to, and damaging, the common optical pathway 130 (e.g., a surgical fiber in the endoscope probe 113). The blast shield 280 can also help scatter the reflected laser beam 148 that travels through the common optical pathway 130, and prevent the reflected laser beam 148 from getting refocused through the lens system and going back into the laser system 102 and interacting with laser emission or otherwise damaging the laser system 102.

FIG. 2B illustrates generally an example of a target identification system 200B, which is a variant of the target identification system 200A. The target identification system 200B can include the probe 113, the spectroscopy system 115, the temperature monitor 152, and a beam splitter 214B which is a variant of the beam splitter 214A of the system 200. The beam splitter 214B includes, among other things, a flat hollow reflector 270, and a lens system between the second port 222 and the hollow reflector 270. In contrast to the lens system of the beam splitter 214A which comprises collimating lens 220 and focusing lens 224, the lens system of the beam splitter 214B includes a biconvex lens 225 having two convex surfaces with respective radii of curvature. In an example, the two convex surfaces have the same radius of curvature. The biconvex lens 225 can converge the laser beam 118 exiting the laser fiber 230, and direct it through the aperture 275 of the flat hollow reflector 270 towards the common optical pathway 130. In some examples, the biconvex lens 225 may include, on its surface facing the hollows reflector 270, a wavelength sensitive material or coating transparent or anti-reflective to the wavelength of the laser but highly reflective to wavelengths of the optical response signal 119, such that the laser energy can be passed through without obstruction, while a portion (if any) of the optical response signal 119 leaking through the aperture 275 of the hollow reflector 270 can be redirected to the third port 223.

Similar to the collimating lens 220 and focusing lens 224, in some instances, certain amount of laser energy 138 may dissipate in the hollow reflector 270 or other optical components and cause component overheating, such as due to coupling anomaly between the laser system 102 and the beam splitter 214B, a misalignment of the laser fiber 230 and the lens system in the beam splitter 214B, or defects of the lens system such as crack, dust, or degradation of the biconvex lens 225. The temperature monitor 152 can continuously or recurrently monitor the temperature of the reflector body via one or more temperature sensors, such as temperature sensors 254 and/or 256, and detect and generate a diagnostic of overheating. An alert or notification of substantial temperature increase and/or the diagnostic of overheating may be generated and presented to a user. Responsive to the detection of component overheating, the overheating protection system 150 can adjust a setting of the laser system, such as shutting down the laser generator 112 temporarily, or change one or more laser beam parameters to reduce laser energy emission, as discussed above with reference to FIG. 2A.

Figure 3A:
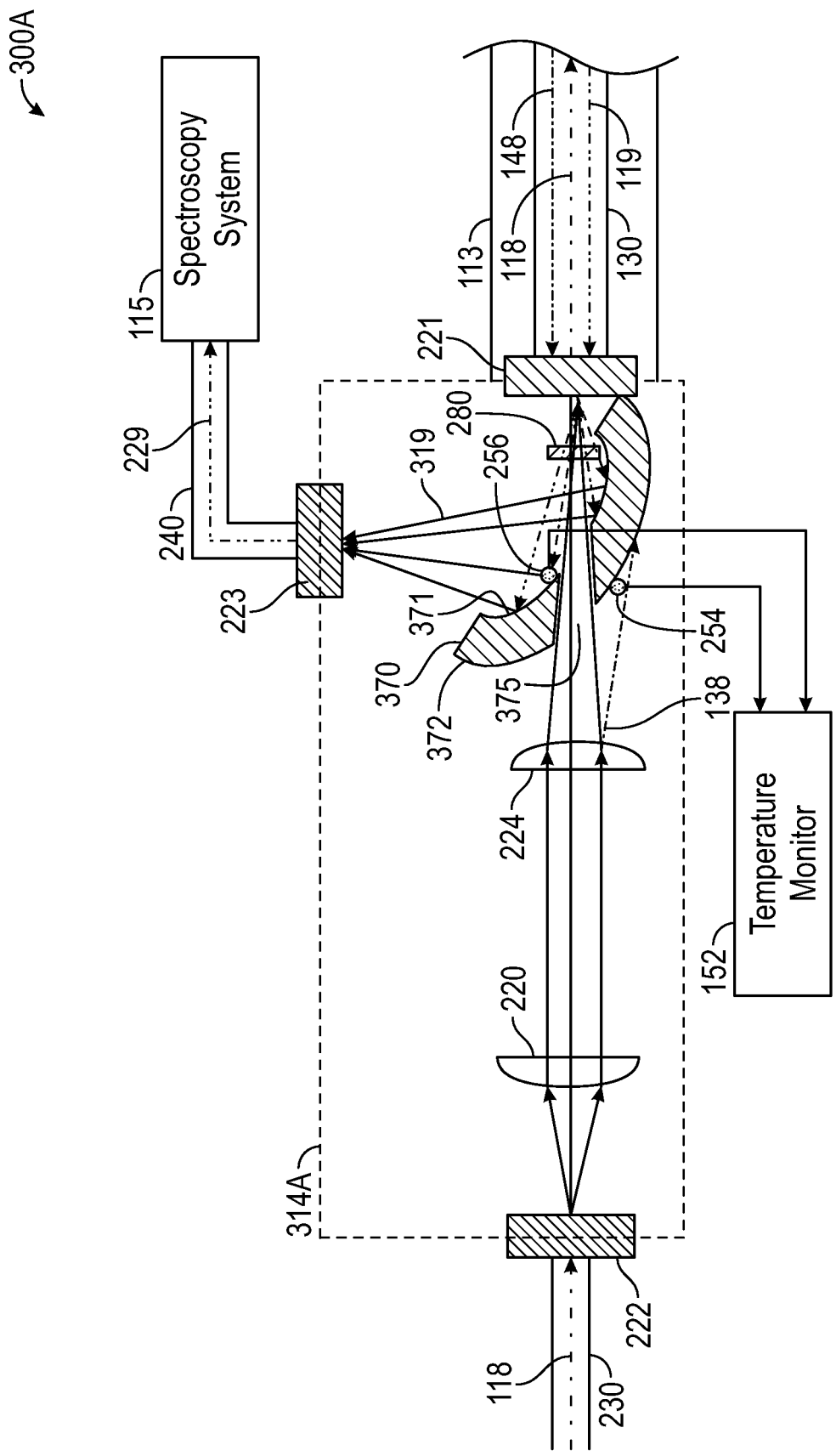
FIGS. 3A-3B illustrate generally example target identification systems each including an optical splitter that comprises a flat hollow reflector.
Figure 3B:
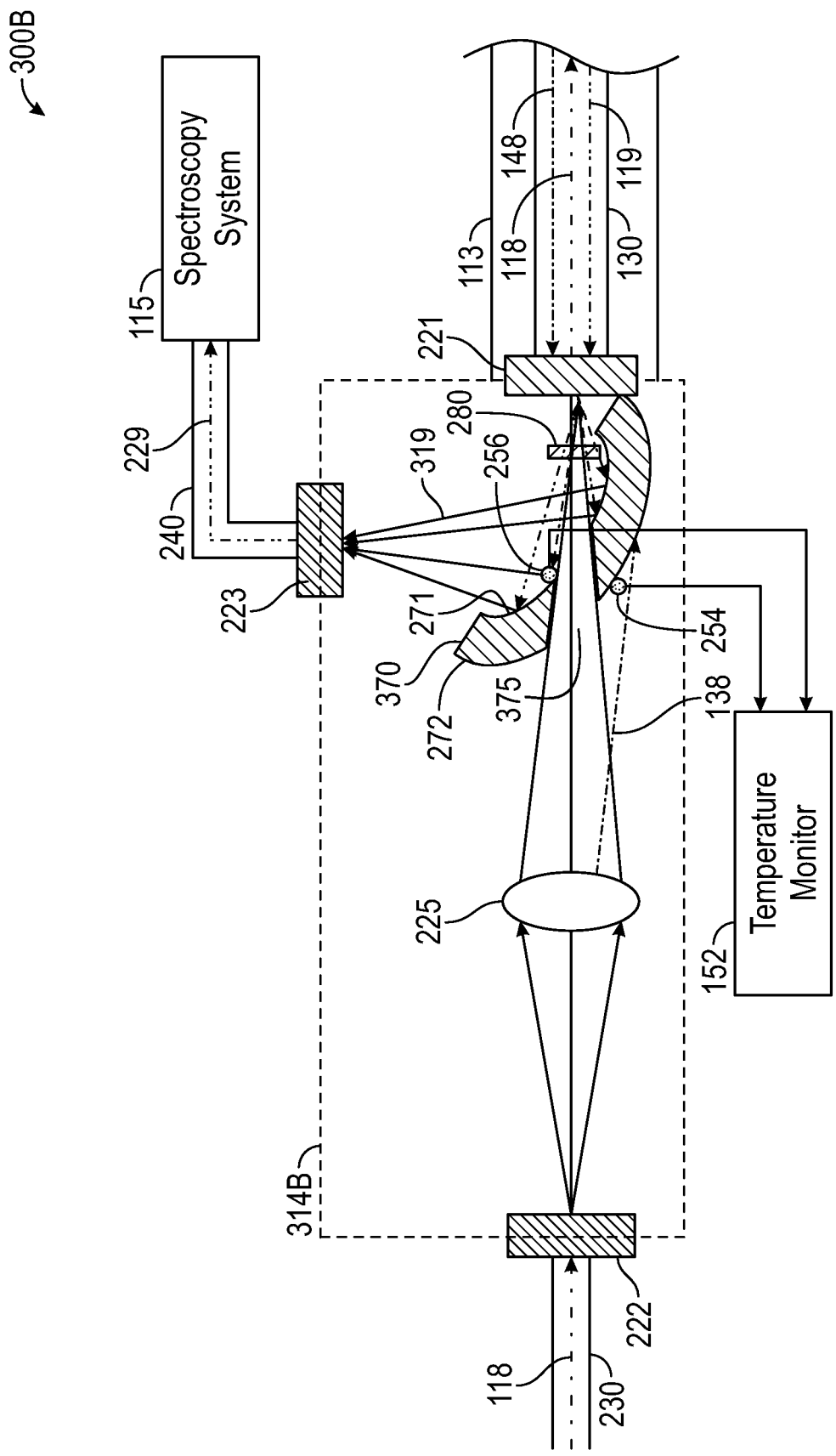

FIGS. 3A-3B illustrate generally example target identification systems each including a beam splitter that comprises a parabolic hollow reflector. A target identification system 300A, as illustrated in FIG. 3A, is a variant of the target identification system 200A, and can include the probe 113, the spectroscopy system 115, the temperature monitor 152, and a beam splitter 314A which is a variant of the beam splitter 214A of the system 200A. The beam splitter 314A includes, among other things, a lens system comprising a collimating lens 220 and a focusing lens 224, and a hollow reflector 370 such as made of metal, glass, or plastic, among other materials. In an example, the hollow reflector 370 is a hollow mirror. In contrast to the flat hollow reflector 270, the hollow reflector 370 is a parabolic reflector comprising a concave reflective surface 371 and a convex nonreflective surface 372. The optical response signal 119, reflected or radiated from the target 117 and traveling back into the beam splitter 314A via the common optical pathway 130, can be coupled from the first port 221 to the third port 223 via the parabolic hollow reflector 370. The concave reflective surface 371 has a specific radius of curvature, and can be positioned to reflect and converge the incoming optical response signal 119, redirect the reflected and converged optical response signal 319 towards the third port 223 of the optical splitter 314A. In some examples, the reflective surface 371 may include a wavelength sensitive material or coating, such as an AR material, that can be transparent or anti-reflective to the wavelength of the laser, but highly reflective to wavelengths of interest of the optical response signal 119. As such, much if not all of the laser energy can be passed from the second port 222 to the first port 221. The reflected and focused optical response signal 319 can transmit to the spectroscopy system 115 via the spectrometer fiber 240. Compared to the beam splitter 214A which uses a flat hollow reflector 270 to reflect the optical response signal 319 and another separate focusing lens 260 to converge the reflected response signal, the parabolic hollow reflector 370 can achieve signal reflection and convergence without additional optical components. This may help simplify system complexity, reduce optical alignment errors, and improve overall system reliability.

Similar to the flat hollow reflector 270, the parabolic hollow reflector 370 can have an aperture 375, such as a through-hole extending through the reflector body. The aperture 375 can be aligned with the collimated and focused laser beam 118, and can be sized, shaped, or otherwise configured to allow the laser beam to pass therethrough without obstruction. In various examples, the aperture 375 can be spatially aligned with the first port 221, such that the laser beam 118 can be directed into the optical pathway 130 via the first port 221. The aperture 375 may be located at substantially the center of the reflector 370. Alternatively, the aperture 375 may be located at other locations of the reflector body away from the center. In some examples, two or more apertures may be included in the body of the parabolic hollow reflector 370, as similarly discussed above with respect to the flat hollow reflector 270. The temperature monitor 152 can continuously or recurrently monitor the temperature of the reflector body via one or more temperature sensors, such as sensors 254 and/or 256, and detect and generate a diagnostic of overheating. An overheating protection system 150 can automatically adjust a setting of the laser system based on the detected temperature increase of the reflector body or the diagnostic of overheating.

FIG. 3B illustrates generally an example of a target identification system 300B, which is a variant of the target identification system 300A. The target identification system 300B can include the probe 113, the spectroscopy system 115, the temperature monitor 152, and a beam splitter 314B which is a variant of the beam splitter 314A of the system 300A. The beam splitter 314B includes, among other things, a parabolic hollow reflector 370, and a lens system between the second port 222 and the hollow reflector 270 that comprises a biconvex lens 225, as similarly included in the system 200B. The biconvex lens 225 can converge the laser beam 118 exiting the laser fiber 230, and direct it through the aperture 375 of the parabolic hollow reflector 370 towards the common optical pathway 130.

As discussed above, in some instances, dissipating laser energy 138 may dissipate in the hollow reflector 370 or other optical components and cause component overheating, such as due to coupling anomaly between the laser system 102 and the beam splitter 214B, a misalignment of the laser fiber 230 and the lens system in the beam splitter 214B, or defects of the lens system such as crack, dust, or degradation of the biconvex lens 225. The temperature monitor 152 can continuously or recurrently monitor the temperature of the reflector body via one or more temperature sensors, such as sensors 254 and/or 256, detect component overheating such as overheating of the hollow reflector 370, and generate an overheating diagnostic. An alert or notification of temperature increase and/or the overheating diagnostic may be generated and presented to a user. The overheating protection system 150 can automatically adjust a setting of the laser system, such as shutting down the laser generator 112 temporarily, or change one or more laser beam parameters to reduce laser energy output.

FIGS. 4A-4B illustrate examples of beam splitters 414A and 414B each including multiple reflectors that collaboratively redirect the optical response signal 119 towards the third port 223, and ultimately into the spectroscopy system 115 via the spectrometer fiber 240. In FIG. 4A, the multiple reflectors include the flat hollow reflector 270 similarly shown in FIGS. 2A-2B, and additional one or more reflectors, such as a flat mirror 410, positioned relative to flat hollow reflector 270 and configured to further reflect the optical signal towards the third port 223. Similarly, in FIG. 4B, the multiple reflectors include the parabolic hollow reflector 370 similarly shown in FIGS. 3A-3B, and additional one or more reflectors, such as a flat mirror 410, positioned relative to parabolic hollow reflector 370 and configured to reflect the optical signal 319 reflected and converged by the parabolic hollow reflector 370 towards the third port 223. The additional one or more reflectors allow more convenient positioning of the third port 223 on the beam splitter and coupling to the spectroscopy system 115.

Figure 5:
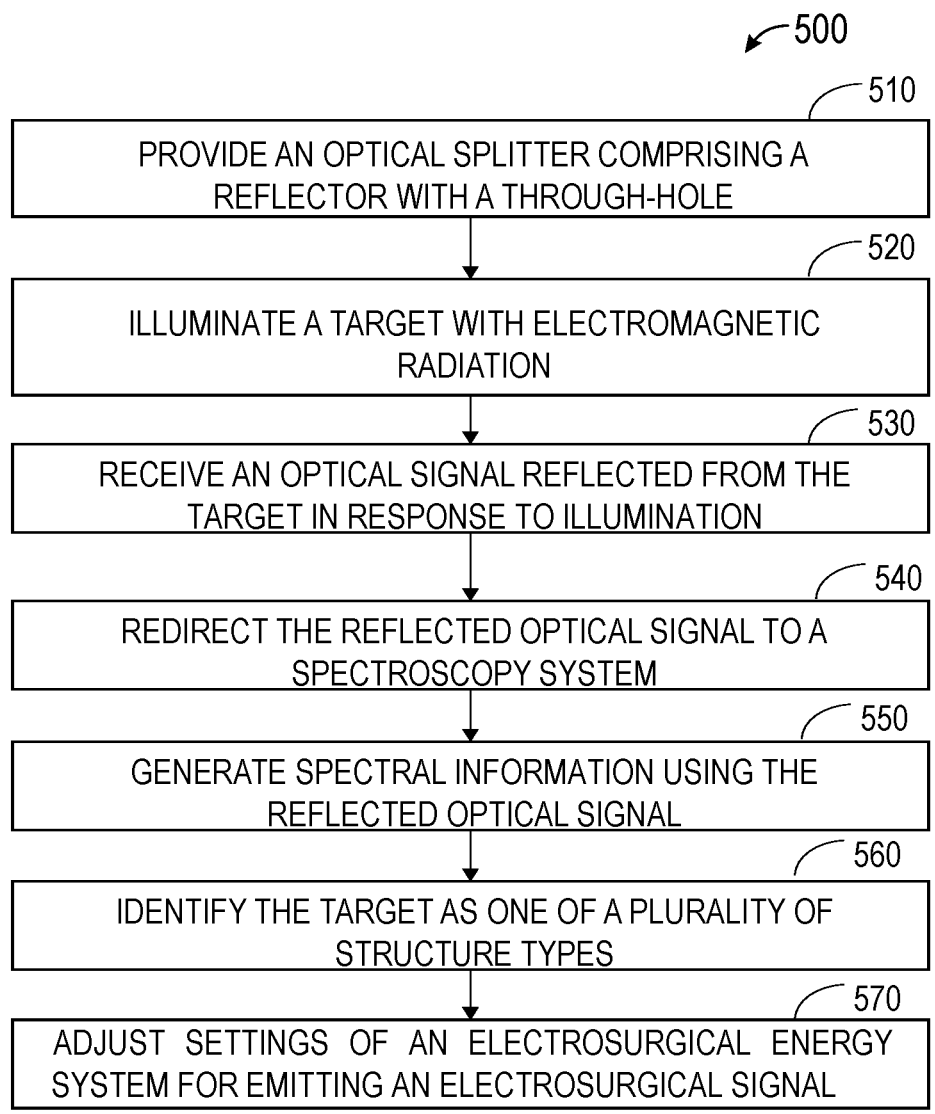
FIG. 5 illustrates generally an example method for identifying a target for treatment in a patient's body.

FIG. 5 is a flow chart illustrating an example method 500 for identifying one or more characteristics of a target and optionally, based thereon, operating, for example, an electrosurgical system (e.g., a laser system) for treatment in a patient's body. The electrosurgical energy may be used to ablate the target, such as an anatomical tissue target (e.g., soft tissue, hard tissue, or abnormal such as cancerous tissue) or a calculi target (e.g., kidney or pancreobiliary or gallbladder stone). The method 500 may be implemented in and executed by the surgical system 110. Although the processes of the method 500 are drawn in one flow chart, they are not required to be performed in a particular order. In various examples, some of the processes can be performed in a different order than that illustrated herein.

At 510, an optical splitter, such as the optical splitter 114 or a variant thereof such as any of the beam splitters 214A, 214B, 314A, 314B, 414A, or 414B, may be provided for use in an electrosurgery. The optical splitter can include a reflector having an aperture, such as a through-hole extending from a reflective surface to a non-reflective surface of the reflector. Examples of such a reflector can include the flat hollow reflector 270 with the aperture 275 in the reflector body, or the parabolic hollow reflector 370 with the aperture 375 in the reflector body, as shown in FIGS. 2A-2B, 3A-3B, and 4A-4B and described above with reference to such figures.

At 520, a target in a subject's body and the surrounding environment can be illuminated with electromagnetic radiation, such as produced by the light source 104. The light source may produce electromagnetic radiation within an optical range from UV to IR. Examples of the electromagnetic radiation include visible light, infrared light, ultraviolet light, or fluorescent light. The electromagnetic radiation may be directed to the target through an optical pathway extending along an elongate body of an endoscope, such as discussed above with reference to FIG. 1. Alternatively, illumination light may be produced by one or more illumination lights (e.g., LEDs) positioned at a distal end of an endoscope.

At 530, an optical signal reflected or radiated from the target in response to the electromagnetic radiation may be received by an endoscope probe. The reflected optical signal can transmit through an optical pathway, such as the common optical pathway 130 within the endoscope probe 103. The probe, and the optical pathway therein, can be optically coupled to the optical splitter. At 540, the reflected optical signal can be reflected by the reflector of the optical splitter, and at least a portion thereof can be redirected to a port of the beam splitter optically coupled to a spectroscopy system, as illustrated in any of FIGS. 2A-2B, 3A-3B, and 4A-4B.

At 550, spectral information indicative of the characteristic(s) (e.g., a type, a material, a composition, a composition profile, a structure or hardness of the anatomical target) of the target may be generated from the reflected optical signal by the spectroscopy system, such as the spectrometer 128. Spectroscopic techniques can be used alone or in combination to analyze hard or soft tissue chemical composition, and create a composition profile using digital spectral data. Examples of the digital spectral data may include a reflectance intensity at a specific wavelength, a statistical feature of reflectance over two or more different wavelengths, a graphical feature of a graphical representation of the reflectance spectrum, among others.

At 560, based the spectral information, the characteristic(s) of the target may be identified using, such as the feedback analyzer 116. In an example, the target includes a calculi target, and the spectral information may be used to identify the calculi target as one of a plurality of calculi types with distinct compositions, such as tones or stone fragments in various stone-forming regions such as urinary system, gallbladder, nasal passages, gastrointestinal tract, stomach, or tonsils. In an example, the calculi target may be identified as one of stone types with distinct chemical compositions, such as one of a CaP stone, a MAP stone, a COM stone, a COD stone, a cystine stone, a cholesterol-based stone, or a uric acid (UA) stone. In another example, the target includes an anatomical tissue target, and the spectral information may be used to identify the anatomical tissue target as one of a plurality of tissue types, such as soft tissue (e.g., muscles, tendons, ligaments, blood vessels, fascia, skin, fat, and fibrous tissues), hard tissue such as bone, connective tissue such as cartilage, among others. In some example, the anatomical tissue target may be identified as one of tissue types with distinct anatomical locations. For example, a renal tissue target may be identified as one of calyx tissue, cortex tissue, medulla tissue, or ureter tissue. In another example, an identified tissue target may be identified as normal tissue or abnormal tissue (e.g., cancerous tissue). In yet another example, an identified tissue target may be identified as treatment area (e.g., tumor or polyp intended for removal) or a non-treatment area (e.g., blood vessels, muscle, etc.).

The spectral information generated at 550, and/or the identification of the target at 560, may be used to control delivery of electrosurgical energy, such as laser energy, to the target. The method 500 can include an optional step 570 of generating a control signal to adjust a setting of an electrosurgical energy system for emitting an electrosurgical signal based on the identification of the target. In an example, the electrosurgical energy system can be the surgical laser system 102, and the control signal may be generated using the feedback analyzer 116 to adjust a setting of the laser system for emitting a laser beam. The electrosurgical signal, such as a laser beam, may be directed, through the aperture of the reflector and the optical pathway of the probe, to the target, as illustrated in and discussed with reference to any of FIGS. 2A-2B, 3A-3B, and 4A-4B. Examples of adjusting the laser settings may include delivering or withhold delivering the laser beam, or adjust a laser beam parameter such as wavelength, power, power density, energy, or a pulse parameter (e.g., pulse width, pulse rate, amplitude, duty cycle, pulse shape), exposure time, total dose or energy, or one or more combinations thereof, among others. In an example, for a calculi target or a portion thereof composed of hard material, the laser system may produce a laser beam with a higher energy to ablate or dust the target. For a calculi target or a portion thereof composed of soft material, the laser system may produce a laser beam with a lower energy to ablate or dust the target.

Figure 6:
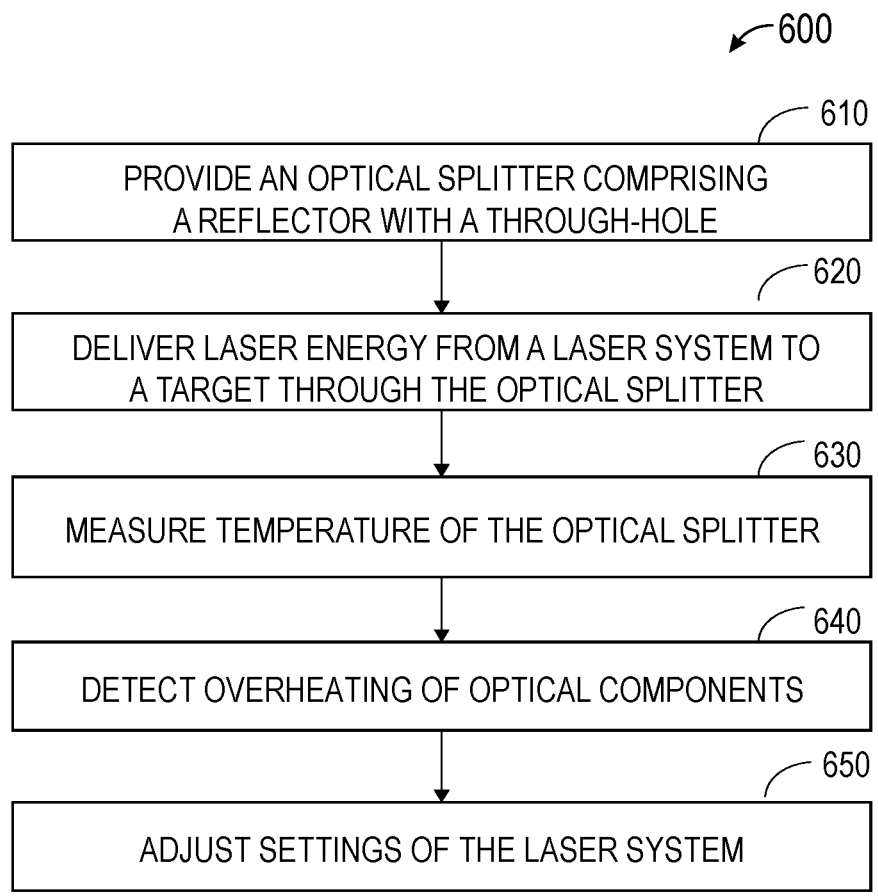
FIG. 6 illustrates generally an example method for monitoring temperature of an optical component of an electrosurgical system and protecting said optical component from overheating.

FIG. 6 is a flow chart illustrating a method 600 for monitoring temperature of an optical component such as one in an optical splitter of an electrosurgical system, and protecting said optical component from overheating during the electrosurgery (e.g., laser ablation of an anatomical tissue target or a calculi target). In an example, the method 600 can be implemented in and executed by the overheating protection system 150 of the surgical system 110.

At 610, an optical splitter may be provided for use in an electrosurgery. Examples of such optical splitter include the optical splitter 114, or a variant thereof such as any of the beam splitters 214A, 214B, 314A, 314B, 414A, or 414B, as shown in FIGS. 2A-2B, 3A-3B, and 4A-4B. The optical splitter can include a reflector having an aperture extending from a reflective surface to a non-reflective surface of the reflector. Examples of such reflector can include the flat hollow reflector 270 with the aperture 275 in the reflector body, or the parabolic hollow reflector 370 with the aperture 375 in the reflector body, as shown in FIGS. 2A-2B, 3A-3B, and 4A-4B.

At 620, laser energy may be produced by a laser system such as the surgical laser system 102, and directed, through the aperture of the reflector and the optical pathway of an endoscope probe optically coupled to the beam splitter, towards the target, as illustrated in any of FIGS. 2A-2B, 3A-3B, and 4A-4B. The laser energy may be used to ablate the target, such as an anatomical tissue target (e.g., soft tissue, hard tissue, or abnormal such as cancerous tissue), or a calculi target (e.g., kidney or pancreobiliary or gallbladder stone).

As described above with reference to FIGS. 2A-2B, 3A-3B, and 4A-4B, although the aperture of the reflector (e.g., the aperture 275 or 375) can allow most of the laser energy to pass therethrough without interacting with the reflector body, in certain occasions some laser energy may dissipate in the reflector body. This may occur, for example, due to a coupling anomaly between the laser system and the beam splitter, a misalignment of the laser fiber and the lens system within the beam splitter (e.g., collimating lens 220 and focusing lens 224, or biconvex lens 225), or defects of the lens system such as crack, dust, or degradation of lens system. Such laser energy dissipation may cause a temperature increase in the non-reflective surface of the reflector body or a portion thereof. Additionally or alternatively, in some instances, a portion of the laser energy incident on the target during the electrosurgery (e.g., ablation of tissue or a calculi target) may get reflected or radiated back to the endoscope probe, scatter onto the reflective surface of the reflector, and cause heat buildup therein. Overheating of the optical components such as the reflector, if not timely corrected or mitigated, may cause damage of those optical components. Continuous or recurrent temperature monitoring can help identify probable causes of overheating, and prevent or reduce damages due to overheating.

At 630, temperature an optical component such as the reflector of the optical splitter may be monitored, such as using the temperature monitor 152. As discussed above, the temperature monitor 152 can be coupled to one or more of the first temperature sensor 254 to sense temperature of the non-reflective surface of the reflector, or a second temperature sensor 256 to sense temperature of the reflective surface of the reflector. In an example, the temperature measurement may be synchronized with the laser pulses to help improve the reliability and sensitivity of detecting temperature change in the reflector.

At 640, reflector overheating may be detected, such as using the temperature monitor 152. In an example, reflector overheating may be detected based on a temperature change during the issuance of laser energy relative to a baseline temperature prior to the issuance of laser energy. For example, a temperature increase in the non-reflective surface, if exceeding a specified threshold, may indicate laser energy dissipating in the non-reflective surface of the reflector. A first diagnostic of coupling anomaly between the laser system and the beam splitter, a misalignment between the laser fiber and the lens system within the beam splitter, or defects of the lens system, may be generated and presented to the user such as via the display 105. Additionally or alternatively, an temperature increase in the reflective surface, if exceeding a specified threshold, may indicate reflected laser energy scattering onto the reflective surface of the reflector. A second diagnostic of misalignment of the optical pathway in the endoscope probe and the beam splitter may be generated and presented to the user such as via the display 105.

In addition or alternative to using only one temperature sensor, in some example, reflector overheating may be detected using differential temperature between the opposite surfaces of the reflector during issuance of laser energy. For example, if the non-reflective surface temperature (as measured by the first temperature sensor) is higher than the reflective surface temperature (as measured by the second temperature sensor) by a first margin, then a first diagnostic of coupling anomaly between the laser system and the beam splitter, a misalignment between the laser fiber and the lens system within the beam splitter, or defects of the lens system, may be generated and presented to the user. If the reflective surface temperature is higher than the non-reflective surface temperature by a second margin, then a second diagnostic of misalignment of the optical pathway in the endoscope probe and the beam splitter may be generated and presented to the user.

The method 600 can include an optional step 650 of adjusting a setting of the laser system in response to the detection of overheated optical component. The adjustment can be controlled automatically by a feedback controller in the overheating protection system 150, as discussed above with reference to FIG. 1. Such adjustment may include, for example, shutting down the laser generator temporarily, or changing one or more laser beam parameters (e.g., laser operation mode such as pulse or continuous wave, power, energy, frequency, pulse shape, pulse profile, or one or more combinations thereof) to reduce laser energy output. In some examples, in response to a diagnostic of misalignment, a recommendation for corrective actions (e.g., adjusting alignment, or replacing a part such as the endoscope probe) may be provided to the user, such as via the display 105.

Figure 7:
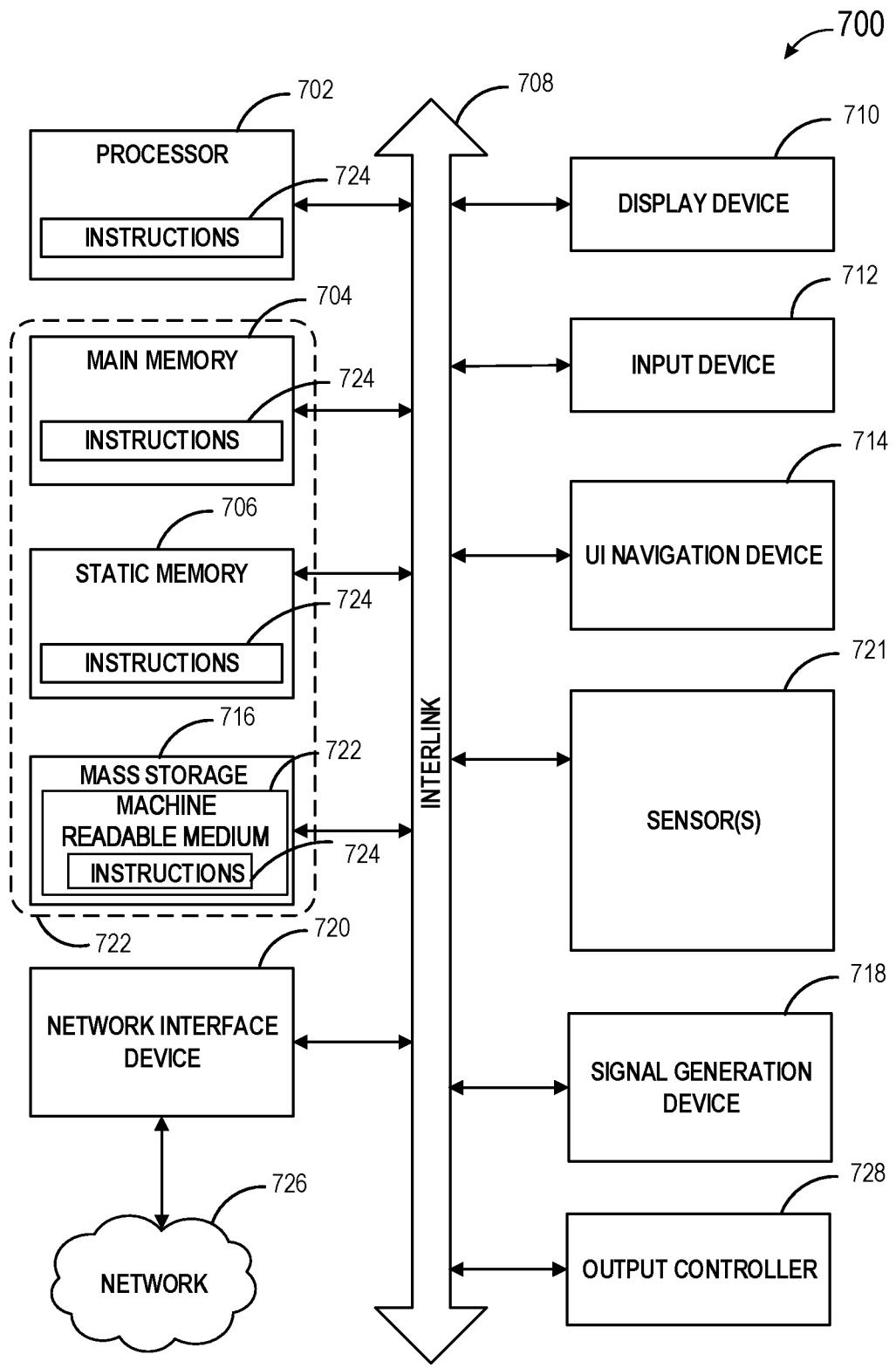
FIG. 7 illustrates generally a block diagram of an example machine 700 upon which any one or more of the techniques (e.g., methodologies) discussed herein may perform.

FIG. 7 illustrates generally a block diagram of an example machine 700 upon which any one or more of the techniques (e.g., methodologies) discussed herein may perform. Portions of this description may apply to the computing framework of various portions of the surgical system 110, such as the spectroscopy system 115 and the overheating protection system 150.

In alternative embodiments, the machine 700 may operate as a standalone device or may be connected (e.g., networked) to other machines. In a networked deployment, the machine 700 may operate in the capacity of a server machine, a client machine, or both in server-client network environments. In an example, the machine 700 may act as a peer machine in peer-to-peer (P2P) (or other distributed) network environment. The machine 700 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 700 may include a hardware processor 702 (e.g., a central processing unit (CPU), a graphics processing unit (GPU), a hardware processor core, or any combination thereof), a main memory 704 and a static memory 706, some or all of which may communicate with each other via an interlink (e.g., bus) 708. The machine 700 may further include a display unit 710 (e.g., a raster display, vector display, holographic display, etc.), an alphanumeric input device 712 (e.g., a keyboard), and a user interface (UI) navigation device 714 (e.g., a mouse). In an example, the display unit 710, input device 712 and UI navigation device 714 may be a touch screen display. The machine 700 may additionally include a storage device (e.g., drive unit) 716, a signal generation device 718 (e.g., a speaker), a network interface device 720, and one or more sensors 721, such as a global positioning system (GPS) sensor, compass, accelerometer, or other sensors. The machine 700 may include an output controller 728, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 716 may include a machine readable medium 722 on which is stored one or more sets of data structures or instructions 724 (e.g., software) embodying or utilized by any one or more of the techniques or functions described herein. The instructions 724 may also reside, completely or at least partially, within the main memory 704, within static memory 706, or within the hardware processor 702 during execution thereof by the machine 700. In an example, one or any combination of the hardware processor 702, the main memory 704, the static memory 706, or the storage device 716 may constitute machine readable media.

While the machine-readable medium 722 is illustrated as a single medium, the term "machine readable medium" may include a single medium or multiple media (e.g., a centralized or distributed database, and/or associated caches and servers) configured to store the one or more instructions 724.

The term "machine readable medium" may include any medium that is capable of storing, encoding, or carrying instructions for execution by the machine 700 and that cause the machine 700 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EPSOM)) and flash memory devices; magnetic disks, such as internal hard disks and removable disks; magneto-optical disks; and CD-ROM and DVD-ROM disks.

The instructions 724 may further be transmitted or received over a communication network 726 using a transmission medium via the network interface device 720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 720 may include one or more physical jacks (e.g., Ethernet, coaxial, or phone jacks) or one or more antennas to connect to the communication network 726. In an example, the network interface device 720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 700, and includes digital or analog communications signals or other intangible medium to facilitate communication of such software.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A surgical system, comprising:
   an electrosurgical or electromagnetic energy system configured to generate an electrosurgical or electromagnetic signal operable to ablate an anatomical target;
   a probe including an optical pathway configured to pass (i) the electrosurgical or electromagnetic signal to the anatomical target and (ii) an optical signal from the anatomical target in response to illumination incident on the anatomical target;
   an optical splitter optically coupled to the probe, the optical splitter being configured to direct the electrosurgical or electromagnetic signal to the optical pathway of the probe, and to receive at least a portion of the optical signal from the optical pathway of the probe and redirect the received at least a portion of the optical signal; and
   a temperature monitor coupled to at least one temperature sensor, the temperature monitor being configured to monitor a temperature of at least a surface of the optical splitter responsive to emission of the electrosurgical or electromagnetic signal, and to generate an overheating diagnostic of the optical splitter based at least in part on the monitored temperature.

2. The surgical system of claim 1, wherein the optical splitter further comprises a reflector having an aperture configured to pass the electrosurgical or electromagnetic signal therethrough, and the at least one temperature sensor is substantially proximate to the aperture.

3. The surgical system of claim 1, wherein the electrosurgical or electromagnetic energy system includes a laser system configured to emit laser pulses, and the temperature monitor is configured to synchronize temperature measurement with the laser pulses.

4. The surgical system of claim 1, wherein: (i) the optical splitter further comprises a reflector, the at least a surface of the splitter includes a non-reflective surface of the reflector; (ii) the at least one temperature sensor includes a temperature sensor on the non-reflective surface of the reflector; and (iii) the temperature monitor is configured to detect a temperature change of the non-reflective surface indicative of at least a portion of the electrosurgical or electromagnetic signal being incident on the non-reflective surface of the reflector, and to generate the overheating diagnostic based at least in part on the detected temperature change of the non-reflective surface.

5. The surgical system of claim 1, wherein: (i) the optical splitter further comprises a reflector, the at least a surface of the splitter includes a reflective surface of the reflector; (ii) the at least one temperature sensor includes a temperature sensor on the reflective surface of the reflector; and (iii) the temperature monitor is configured to detect a temperature change of the reflective surface indicative of at least a portion of the electrosurgical or electromagnetic signal reflected from the anatomical target and incident on the reflective surface of the reflector, and to generate the overheating diagnostic based at least in part on the detected temperature change of the reflective surface.

6. The surgical system of claim 1, wherein: (i) the optical splitter further comprises a reflector, the at least a surface of the splitter includes a non-reflective surface and a reflective surface of the reflector; (ii) the at least one temperature sensor includes a first temperature sensor configured to sense a temperature of the non-reflective surface of the reflector opposite to the reflective surface, and a second temperature sensor configured to sense a temperature of the reflective surface; and (iii) the temperature monitor is configured to generate the overheating diagnostic based at least in part on a comparison between the temperature of the non-reflective surface and the temperature of the reflective surface.

7. The surgical system of claim 6, wherein the overheating diagnostic includes:
    a first indicator of misalignment of the probe and the optical splitter if the temperature of the reflective surface is higher than the temperature of the non-reflective surface; and
    a second indicator of misalignment of the optical splitter and the electrosurgical or electromagnetic energy system if the temperature of the non-reflective surface is higher than the temperature of the reflective surface.

8. The surgical system of claim 1, further comprising a controller circuit configured to generate a control signal to adjust a setting of the electrosurgical or electromagnetic energy system based at least in part on the monitored temperature.

9. A method for operating a surgical system comprising an optical splitter and a probe coupled thereto, the method comprising:
    directing an electrosurgical or electromagnetic signal to an anatomical target through the optical splitter and the probe;
    receiving at least a portion of an optical signal reflected from the anatomical target in response to an illumination of the anatomical target;
    redirecting, via the optical splitter, the received at least a portion of the optical signal;
    monitoring a temperature of at least a surface of the optical splitter via a temperature sensor in response to emission of the electrosurgical or electromagnetic signal; and
    upon determining that the monitored temperature exceeds a predetermined threshold, generating an overheating diagnostic of the optical splitter based at least in part on the monitored temperature.

10. The method of claim 9, wherein the electrosurgical or electromagnetic signal incudes laser pulses, the method further comprising synchronizing the temperature monitoring with the laser pulses.

11. The method of claim 9, wherein: the at least a surface of the splitter includes a surface of a reflector in the optical splitter; monitoring the temperature of the at least a surface of the optical splitter includes detecting a temperature change of the surface of the reflector, the temperature change indicative of at least a portion of the electrosurgical or electromagnetic signal being incident on the reflector; and generating the overheating diagnostic is based at least in part on the detected temperature change.

12. The method of claim 11, wherein detecting the temperature change of the surface of the reflector includes detecting a temperature change on at least one of a reflective surface or a non-reflective surface of the reflector.

13. The method of claim 9, wherein:
    monitoring the temperature of the at least a surface of the optical splitter includes detecting a first temperature of a non-reflective surface of a reflector in the optical splitter, and detecting a second temperature of a reflective surface of the reflector opposite to the non-reflective surface; and
    generating the overheating diagnostic is based at least in part on a comparison between the first temperature and the second temperature.

14. The method of claim 13, wherein the overheating diagnostic includes:
    a first indicator of misalignment of the optical splitter and the probe, if the second temperature is higher than the first temperature; and
    a second indicator of misalignment of the optical splitter and an electrosurgical or electromagnetic energy system generating the electrosurgical or electromagnetic signal, if the first temperature is higher than the second temperature.

15. The method of claim 9, wherein the electrosurgical or electromagnetic signal is generated by an electrosurgical or electromagnetic energy system, the method further comprising adjusting a setting of the electrosurgical or electromagnetic energy system based at least in part on the monitored temperature.

* * * * *

UNITED STATES PATENT AND TRADEMARK OFFICE
CERTIFICATE OF CORRECTION

| | | |
|---|---|---|
| PATENT NO. | : 11,406,449 B1 | Page 1 of 1 |
| APPLICATION NO. | : 17/376908 | |
| DATED | : August 9, 2022 | |
| INVENTOR(S) | : Bukesov et al. | |

It is certified that error appears in the above-identified patent and that said Letters Patent is hereby corrected as shown below:

In the Claims

In Column 26, Line 50, in Claim 4, after "wherein:", insert a linebreak

In Column 26, Line 52, in Claim 4, after "reflector;", insert a linebreak

In Column 26, Line 54, in Claim 4, after "and", insert a linebreak

In Column 26, Line 62, in Claim 5, after "wherein:", insert a linebreak

In Column 26, Line 64, in Claim 5, after "reflector;", insert a linebreak

In Column 26, Line 66, in Claim 5, after "and", insert a linebreak

In Column 27, Line 7, in Claim 6, after "wherein:", insert a linebreak

In Column 27, Line 10, in Claim 6, after "reflector;", insert a linebreak

In Column 27, Line 15, in Claim 6, after "and", insert a linebreak

In Column 28, Line 6, in Claim 10, delete "incudes" and insert --includes-- therefor In Column 28, Line 9, in Claim 11, after "wherein:", insert a linebreak In Column 28, Line 11, in Claim 11, after "splitter;", insert a linebreak In Column 28, Line 15, in Claim 11, after "and", insert a linebreak Signed and Sealed this
Sixteenth Day of May, 2023

*Katherine Kelly Vidal*

Katherine Kelly Vidal
*Director of the United States Patent and Trademark Office*